United States Patent [19]

Blakely et al.

[11] Patent Number: 5,418,162
[45] Date of Patent: May 23, 1995

[54] SEROTONIN TRANSPORTER CDNA

[75] Inventors: Randy D. Blakely, Stone Mountain, Ga.; Marc G. Caron, Ga.; Robert T. Fremeau, Jr., both of Durham, N.C.

[73] Assignees: Duke University, Durham, N.C.; Emory University, Atlanta, Ga.

[21] Appl. No.: 959,943

[22] Filed: Oct. 14, 1992

Related U.S. Application Data

[63] Continuation-in-part of Ser. No. 778,231, Oct. 22, 1991, abandoned.

[51] Int. Cl.$^6$ .......................... C07H 15/00; C12N 1/00
[52] U.S. Cl. ........................ 435/252.3; 435/6; 435/320.1; 435/240.1; 536/24.31; 536/23.5
[58] Field of Search ............... 536/27; 435/172.3, 69.1, 435/240.2, 240.4, 252.3

[56] References Cited

U.S. PATENT DOCUMENTS

| | | | |
|---|---|---|---|
| 4,675,285 | 6/1987 | Clark et al. | |
| 4,745,051 | 5/1988 | Smith et al. | 435/69.1 |
| 5,188,954 | 2/1993 | Lam et al. | 435/6 |

OTHER PUBLICATIONS

R. Radian et al., *J. Biol. Chem.* 25, 15437–15441 (1986).
N. Danbolt et al., *Biochemistry* 29, 6734–6740 (1990).
B. Lopez-Corcuera and C. Aragon, *Eur. J. Biochem.* 181, 519–524 (1989).
J. Guastella et al., *Science* 249, 1303–1306 (1990).
H. Nelson et al., *FEBS Lettr.* 269, 181–184 (1990).
T. Pacholczyk et al. *Nature* 350, 350–354 (1991).
S. Stengelin et al., *The EMBO Journal* 7, No. 4, 1053–1059 (1988).
R. Blakely et al., *Nature* 354, 66–70 (1991).
S. Langer and A.-M. Galzin, *Experimentia* 44, 127–130 (1988).

*Primary Examiner*—Robert A. Wax
*Assistant Examiner*—David Schmickel
*Attorney, Agent, or Firm*—Bell, Seltzer, Park & Gibson

[57] ABSTRACT

Isolated DNA encoding a serotonin transporter is disclosed. Also disclosed are vectors and host cells containing the aforesaid DNA, methods of using the same, purified protein by the same, and oligonucleotides and antibodies which bind thereto. Specific embodiments are cDNAs encoding rat and human serotonin transporter.

15 Claims, 2 Drawing Sheets

SEROTONIN TRANSPORTER CDNA

This invention was made with Government support under Grant No. DA07390-01 from the National Institute of Drug Abuse and Grant Nos. NS-15976, IP53-MH-4421, and MH-40158 from the National Institutes of Health. The Government has certain rights to this invention.

Related Applications

This application is a continuation-in-part of application Ser. No. 07/778,231 filed Oct. 22, 1991 now abandoned.

FIELD OF THE INVENTION

This invention relates to a cDNA clone encoding a serotonin transporter protein, vectors containing this clone, host cells which express this clone, and methods of using the same.

BACKGROUND OF THE INVENTION

Selective antagonism of serotonin (5-hydroxytryptamine, 5HT) and noradrenaline (NA) transport by antidepressants is a key element to our current understanding of human behavioral disorders. See H. Ashton, *Brain Systems, Disorders, and Psychotropic Drugs*, 283–330 (Oxford University Press, New York, 1987). In several studies, 5HT uptake and/or transport sites have been found to be reduced in platelets of patients suffering from depression and reduced in post-mortem brain samples of depressed patients and suicide victims. See generally H. Meltzer, et al., *Arch. Gen. Psychiat.* 38, 1322–1326 (1981); B. Suranyi-Cadotte et al., *Life Sci.* 36, 795–799; M. Briley et al., *Science* 209, 303–305; S. Paul et al., *Arch. Gen. Psych.* 38, 1315–1317 (1981); E. Perry et al., *Brit. J. Psych.* 142, 188–192 (1983); M. Stanley et al., *Science* 216, 1337–1339 (1982). A better understanding of these transporter proteins would provide a better understanding of these behavioral disorders.

Despite decades of study, only the more abundant amino acid neurotransmitter (Glu, GABA, Gly) transporters have been reconstituted after solubilization in an active state. See R. Radian et al., *J. Biol. Chem.* 25, 15437–15441 (1986); N. Danbolt et al., *Biochemistry* 29, 6734–6740 (1990); B. Lopez-Corcuera & C. Aragon, *Eur. J. Biochem.* 181, 519–524 (1989). Recently, GABA (rGAT1) and NA (hNAT) transporters have been cloned, revealing single, structurally-related polypeptides forming each carrier. See J. Guastella et al., *Science* 249, 1303–1306 (1990); H. Nelson et al., *FEBS Lett.* 269, 181–184 (1990); T. Pacholczyk et al., *Nature* 350, 350–354 (1991). The inferred amino acid sequence of both GABA and NA transporters predicts ~12 transmembrane domains, with one large extracellular loop bearing multiple sites for N-linked glycosylation. The structure of the putative seratonin transporter, however, has heretofore remained unknown. Accordingly, an object of the present invention is to provide a cDNA encoding a serotonin transporter and elucidate the structure thereof.

SUMMARY OF THE INVENTION

A first aspect of the present invention is isolated DNA encoding a serotonin transporter selected from the group consisting of: (a) isolated DNA which encodes rat serotonin transporter; (b) isolated DNA which hybridizes to isolated DNA of (a) above and which encodes a serotonin transporter; and (c) isolated DNA differing from the isolated DNAs of (a) and (b) above in codon sequence due to the degeneracy of the genetic code, and which encodes a serotonin transporter. In another respect, the present invention provides isolated DNA consisting essentially of isolated DNA encoding a serotonin transporter, preferably a mammalian serotonin transporter such as the human and rat serotonin transporters. Thus a specific embodiment of the foregoing is isolated DNA encoding a human serotonin transporter selected from the group consisting of: (a) isolated DNA which encodes the human serotonin transporter having the sequence given herein as SEQ ID NO:10; (b) isolated DNA which hybridizes to the isolated human DNA of (a) above and which encodes a human serotonin transporter; and (c) isolated human DNA differing from the isolated DNAs of (a) and (b) above in codon sequence due to the degeneracy of the genetic code, and which encodes a serotonin transporter.

A second aspect of the present invention is a recombinant DNA sequence comprising vector DNA and a DNA encoding a serotonin transporter as given above.

A third aspect of the present invention is a host cell containing a recombinant DNA sequence as given above. Host cells which express the serotonin transporter may be used in the assay procedure discussed below, either lysed to provide cell membranes or as whole cells.

A fourth aspect of the present invention is an aqueous solution containing cell membranes, the cell membranes containing a serotonin transporter, wherein the cell membranes are free of other undesired neurotransmitter transporters such as the noradrenaline transporter.

A fifth aspect of the present invention is an assay procedure comprising the steps of, first, providing an aqueous solution containing cell membranes as given above; then adding a test compound to the aqueous solution; and then monitoring the interaction of the test compound with the serotonin transporter (e.g., by (a) monitoring the transport of serotonin by the serotonin transporter; or (b) monitoring the binding of the test compound to the serotonin transporter). The cell membranes may be those of whole cells or lysed cells. The assay is useful for identifying serotonin transport inhibitors.

A sixth aspect of the present invention is an oligonucleotide probe capable of selectively hybridizing to a DNA comprising a portion of a gene coding for a serotonin transporter. Preferably the probe does not hybridize to a gene coding for other neurotransmitter transporters such as the noradrenaline transporter.

A seventh aspect of the present invention is isolated and purified serotonin transporter protein which is coded for by DNA selected from the group consisting of: (a) isolated DNA which encodes rat serotonin transporter; (b) isolated DNA which hybridizes to isolated DNA of (a) above and which encodes a serotonin transporter; and (c) isolated DNA differing from the isolated DNAs of (a) and (b) above in codon sequence due to the degeneracy of the genetic code, and which encodes a serotonin transporter.

An eighth aspect of the present invention is antibodies (preferably monoclonal antibodies) which bind selectively to the serotonin transporter protein.

The foregoing and other objects and aspects of the present invention will be made apparent from the drawings herein and the specification set forth below.

DETAILED DESCRIPTION OF THE INVENTION

Figure 1A:
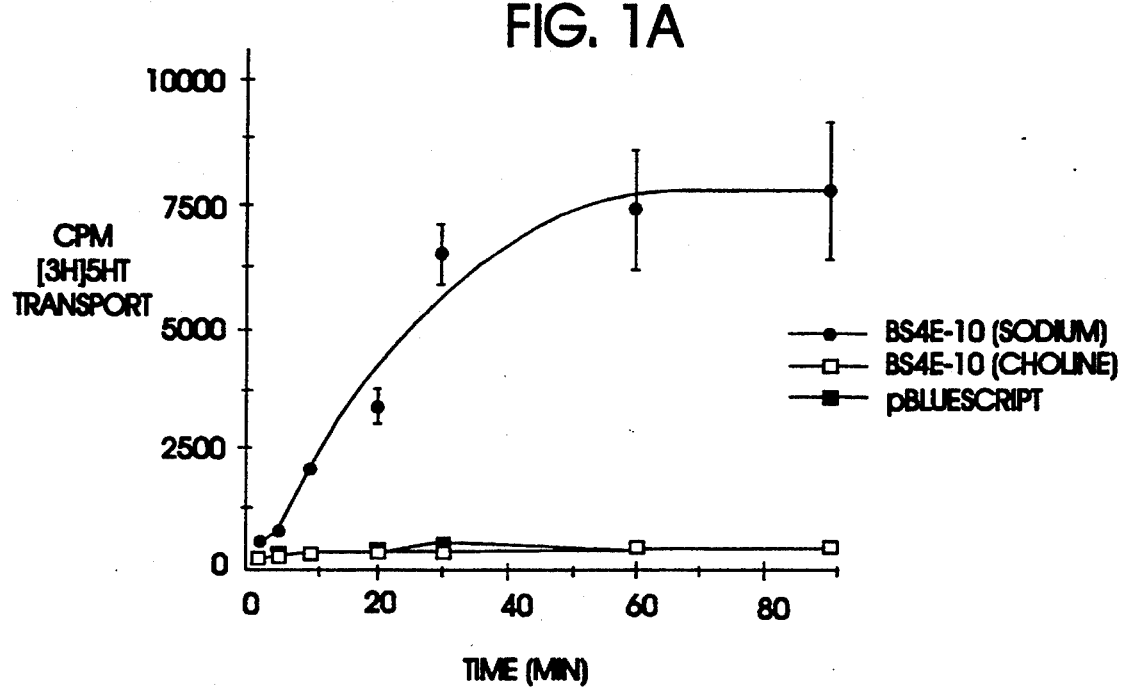
FIG. 1a shows the presence of sodium-dependent 5HT transport in HeLa fibroblasts transfected with BS4E-10 cDNA, which encodes the rat serotonin transporter (rSERT).

Amino acid sequences disclosed herein are presented in the amino to carboxy direction, from left to right. The amino and carboxy groups are not presented in the sequence. Nucleotide sequences are presented herein by single strand only, in the 5' to 3' direction, from left to right. Nucleotides and amino acids are represented herein in the manner recommended by the IUPAC-IUB Biochemical Nomenclature Commission, or (for amino acids) by three letter code, in accordance with 37 CFR §1.822 and established usage. See, e.g., PatentIn User Manual, 99–102 (Nov. 1990)(U.S. Patent and Trademark Office, Office of the Assistant Commissioner for Patents, Washington, D.C. 20231); U.S. Pat. No. 4,871,670 to Hudson et al. at Col. 3 lines 20–43 (applicants specifically intend that the disclosure of this and all other patent references cited herein be incorporated herein by reference).

Serotonin transporters of the present invention include proteins homologous to, and having essentially the same biological properties as, the proteins coded for by the nucleotide sequence set forth as SEQ ID NO:6, SEQ ID NO:8 or SEQ ID NO:10. This definition is intended to encompass natural allelic variations in the serotonin transporter sequence, but to exclude the noradrenaline transporter sequence. Cloned genes of the present invention may code for serotonin transporters of any species of origin, including mouse, rat, rabbit, cat, and human, but preferably code for receptors of mammalian origin. Thus, DNA sequences which hybridize to the sequences given in SEQ ID NO:6, SEQ ID NO:8 or SEQ ID NO:10 and which code for expression of a serotonin transporter are also an aspect of this invention. Conditions which will permit other DNA sequences which code for expression of a serotonin transporter to hybridize to the sequences given in SEQ ID NO:6, SEQ ID NO:8 or SEQ ID NO:10 can be determined in a routine manner. For example, hybridization of such sequences may be carried out under conditions of reduced stringency or even stringent conditions (e.g., conditions represented by a wash stringency of 0.3 Molar NaCl, 0.03M sodium citrate, 0.1% SDS at 60° C. or even 70° C.) to DNA encoding the rat or human serotonin transporter disclosed herein in a standard in situ hybridization assay. See J. Sambrook et al., *Molecular Cloning, A Laboratory Manual,* 2d Ed. (Cold Spring Harbor Laboratory 1989). In general, sequences which code for a serotonin transporter and hybridize to the DNA encoding the rat or human serotonin transporter disclosed herein will be at least 75% homologous, 85% homologous, or even 95% homologous or more with the sequence of the DNA encoding rat or human serotonin transporter disclosed herein. Determinations of homology are made with the two sequences (nucleic acid or amino acid) aligned for maximum matching. Gaps in either of the two sequences being matched are allowed in maximizing matching. Gap lengths of 10 or fewer are preferred, gap lengths of 5 or fewer are more preferred, and gap lengths of 2 or fewer still more preferred.

Further, DNA sequences which code for polypeptides coded for by the sequence given in SEQ ID NO:6, SEQ ID NO:8 or SEQ ID NO:10 or sequences which hybridize thereto and code for a serotonin transporter, but which differ in codon sequence from these due to the degeneracy of the genetic code, are also an aspect of this invention. The degeneracy of the genetic code, which allows different nucleic acid sequences to code for the same protein or peptide, is well known in the literature. See, e.g., U.S. Pat. No. 4,757,006 to Toole et al. at Col. 2, Table 1.

The production of cloned genes, recombinant DNA, vectors, host cells, proteins and protein fragments by genetic engineering techniques is well known. See, e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12; and U.S. Pat. No. 4,879,224 to Wallner at Col. 6 line 8 to Col. 8 line 59.

DNA which encodes the serotonin transporter may be obtained, in view of the instant disclosure, by chemical synthesis, by screening reverse transcripts of mRNA from appropriate cells or cell line cultures, by screening genomic libraries from appropriate cells, or by combinations of these procedures, as illustrated below. Screening of mRNA or genomic DNA may be carried out with oligonucleotide probes generated from the serotonin transporter gene sequence information provided herein. Probes may be labeled with a detectable group such as a fluorescent group, a radioactive atom or a chemiluminescent group in accordance with known procedures and used in conventional hybridization assays, as described in greater detail in the Examples below. In the alternative, serotonin transporter gene sequences may be recovered by use of the polymerase chain reaction (PCR) procedure, with the PCR oligonucleotide primers being produced from the serotonin transporter nucleotide sequence provided herein (particularly from poorly conserved regions thereof). See U.S. Pat. No. 4,683,195 to Mullis et al. and U.S. Pat. No. 4,683,202 to Mullis.

The serotonin transporter may be synthesized in host cells transformed with vectors containing DNA encoding the serotonin transporter. A vector is a replicable DNA construct. Vectors are used herein either to amplify DNA encoding the serotonin transporter and/or to express DNA which encodes the serotonin transporter. An expression vector is a replicable DNA construct in which a DNA sequence encoding the serotonin transporter is operably linked to suitable control sequences capable of effecting the expression of the serotonin transporter in a suitable host. The need for such control sequences will vary depending upon the host selected and the transformation method chosen.

Generally, control sequences include a transcriptional promoter, an optional operator sequence to control transcription, a sequence encoding suitable mRNA ribosomal binding sites, and sequences which control the termination of transcription and translation. Amplification vectors do not require expression control domains. All that is needed is the ability to replicate in a host, usually conferred by an origin of replication, and a selection gene to facilitate recognition of transformants.

Vectors useful for practicing the present invention include plasmids, viruses (including phage), retroviruses, and integratable DNA fragments (i.e., fragments integratable into the host genome by homologous recombination). The vector replicates and functions independently of the host genome, or may, in some instances, integrate into the genome itself. Suitable vectors will contain replicon and control sequences which are derived from species compatible with the intended expression host. Transformed host cells are cells which have been transformed or transfected with the serotonin transporter vectors constructed using recombinant DNA techniques. Transformed host cells ordinarily express the serotonin transporter, but host cells transformed for purposes of cloning or amplifying the serotonin transporter DNA need not express the serotonin transporter. When expressed, the serotonin transporter will typically be located in the host cell membrane.

DNA regions are operably linked when they are functionally related to each other. For example: a promoter is operably linked to a coding sequence if it controls the transcription of the sequence; a ribosome binding site is operably linked to a coding sequence if it is positioned so as to permit translation. Generally, operably linked means contiguous and, in the case of leader sequences, contiguous and in reading phase.

Suitable host cells include prokaryotes, yeast cells or higher eukaryotic cells. Prokaryotes include gram negative or gram positive organisms, for example *Escherichia coli* (*E. coli*) or *Bacilli*. Higher eukaryotic cells include established cell lines of mammalian origin as described below. Exemplary host cells are *E. coli* W3110 (ATCC 27,325), *E. coli* B, *E. coli* X1776 (ATCC 31,537), and *E. coli* 294 (ATCC 31,446). *Pseudomonas* species, *Bacillus* species, and *Serratia marcesans* are also suitable.

A broad variety of suitable microbial vectors are available. Generally, a microbial vector will contain an origin of replication recognized by the intended host, a promoter which will function in the host and a phenotypic selection gene such as a gene encoding proteins conferring antibiotic resistance or supplying an autotrophic requirement. Similar constructs will be manufactured for other hosts. *E. coli* is typically transformed using pBR322. See Bolivar et al., *Gene* 2, 95 (1977). pBR322 contains genes for ampicillin and tetracycline resistance and thus provides easy means for identifying transformed cells.

Expression vectors should contain a promoter which is recognized by the host organism. This generally means a promoter obtained from the intended host. Promoters most commonly used in recombinant microbial expression vectors include the beta-lactamase (penicillinase) and lactose promoter systems (Chang et al., *Nature* 275, 615 (1978); and Goeddel et al., *Nature* 281, 544 (1979), a tryptophan (trp) promoter system (Goeddel et al., *Nucleic Acids Res.* 8, 4057 (1980) and EPO App. Publ. No. 36,776) and the tac promoter (H. De Boer et al., *Proc. Natl. Acad. Sci. USA* 80, 21 (1983)).

While these are commonly used, other microbial promoters are suitable. Details concerning nucleotide sequences of many have been published, enabling a skilled worker to operably ligate them to DNA encoding the serotonin transporter in plasmid or viral vectors (Siebenlist et al., *Cell* 20, 269 (1980)). The promoter and Shine-Dalgarno sequence (for prokaryotic host expression) are operably linked to the DNA encoding the serotonin transporter, i.e., they are positioned so as to promote transcription of the serotonin transporter messenger RNA from the DNA.

Eukaryotic microbes such as yeast cultures may be transformed with suitable serotonin transporter-encoding vectors. See, e.g., U.S. Pat. No. 4,745,057. *Saccharomyces cerevisiae* is the most commonly used among lower eukaryotic host microorganisms, although a number of other strains are commonly available. Yeast vectors may contain an origin of replication from the 2 micron yeast plasmid or an autonomously replicating sequence (ARS), a promoter, DNA encoding the serotonin transporter, sequences for polyadenylation and transcription termination, and a selection gene. An exemplary plasmid is YRp7, (Stinchcomb et al., *Nature* 282, 39 (1979); Kingsman et al., *Gene* 7, 141 (1979); Tschemper et al., *Gene* 10, 157 (1980)). This plasmid contains the trp1 gene, which provides a selection marker for a mutant strain of yeast lacking the ability to grow in tryptophan, for example ATCC No. 44076 or PEP4-1 (Jones, *Genetics* 85, 12 (1977)). The presence of the trp1 lesion in the yeast host cell genome then provides an effective environment for detecting transformation by growth in the absence of tryptophan.

Suitable promoting sequences in yeast vectors include the promoters for metallothionein, 3-phosphoglycerate kinase (Hitzeman et al., *J. Biol. Chem.* 255, 2073 (1980) or other glycolytic enzymes (Hess et al., *J. Adv. Enzyme Reg.* 7, 149 (1968); and Holland et al., *Biochemistry* 17, 4900 (1978)), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are further described in R. Hitzeman et al., EPO Publn. No. 73,657.

Other promoters, which have the additional advantage of transcription controlled by growth conditions, are the promoter regions for alcohol dehydrogenase 2, isocytochrome C, acid phosphatase, degradative enzymes associated with nitrogen metabolism, and the aforementioned metallothionein and glyceraldehyde-3-phosphate dehydrogenase, as well as enzymes responsible for maltose and galactose utilization. In constructing suitable expression plasmids, the termination sequences associated with these genes may also be ligated into the expression vector 3' of the the serotonin transporter coding sequences to provide polyadenylation and termination of the mRNA.

Cultures of cells derived from multicellular organisms are a desirable host for recombinant serotonin transporter synthesis. In principal, any higher eukaryotic cell culture is workable, whether from vertebrate or invertebrate culture, including insect cells. However, mammalian cells are preferred, as illustrated in the Examples. Propagation of such cells in cell culture has become a routine procedure. See Tissue Culture, Academic Press, Kruse and Patterson, editors (1973). Examples of useful host cell lines are VERO and HeLa cells, Chinese hamster ovary (CHO) cell lines, and WI138, BHK, COS-7, CV, and MDCK cell lines. Expression vectors for such cells ordinarily include (if necessary) an origin of replication, a promoter located upstream from the gene to be expressed, along with a ribosome binding site, RNA splice site (if intron-containing genomic DNA is used), a polyadenylation site, and a transcriptional termination sequence.

The transcriptional and translational control sequences in expression vectors to be used in transforming vertebrate cells are often provided by viral sources. For example, commonly used promoters are derived from polyoma, Adenovirus 2, and Simian Virus 40 (SV40). See, e.g., U.S. Pat. No. 4,599,308. The early and late promoters are useful because both are obtained easily from the virus as a fragment which also contains the SV40 viral origin of replication. See Fiers et al., *Nature* 273, 113 (1978). The vaccinia virus may be used as a vector, as described in the Examples. Further, the serotonin transporter promoter, control and/or signal sequences, may also be used, provided such control sequences are compatible with the host cell chosen.

An origin of replication may be provided either by construction of the vector to include an exogenous origin, such as may be derived from SV40 or other viral source (e.g. Polyoma, Adenovirus, VSV, or BPV), or may be provided by the host cell chromosomal replication mechanism. If the vector is integrated into the host cell chromosome, the latter may be sufficient.

Rather than using vectors which contain viral origins of replication, one can transform mammalian cells by the method of cotransformation with a selectable marker and the serotonin transporter DNA. An example of a suitable selectable marker is dihydrofolate reductase (DHFR) or thymidine kinase. See U.S. Pat. No. 4,399,216. Such markers are proteins, generally enzymes, that enable the identification of transformant cells, i.e., cells which are competent to take up exogenous DNA. Generally, identification is by survival of transformants in culture medium that is toxic, or from which the cells cannot obtain critical nutrition without having taken up the marker protein.

Host cells such as insect cells (e.g., cultured *Spodoptera frugiperda* cells) and expression vectors such as the baculovirus expression vector (e.g., vectors derived from *Autographa californica* MNPV, *Trichoplusia ni* MNPV, *Rachiplusia ou* MNPV, or *Galleria ou* MNPV) may be employed in carrying out the present invention, as described in U.S. Pat. Nos. 4,745,051 and 4,879,236 to Smith et al. In general, a baculovirus expression vector comprises a baculovirus genome containing the gene to be expressed inserted into the polyhedrin gene at a position ranging from the polyhedrin transcriptional start signal to the ATG start site and under the transcriptional control of a baculovirus polyhedrin promoter.

Serotonin transporter made from cloned genes in accordance with the present invention may be used for screening compounds for their ability to interact with the serotonin transporter, such as for transporter inhibitory activity or competitive binding thereto, or for determining the amount of an inhibitory drug in a solution (e.g., blood plasma or serum). For example, host cells may be transformed with a vector of the present invention, serotonin transporter expressed in that host and the cells used whole to screen compounds for serotonin transporter inhibition activity. In another example, host cells may be transformed with a vector of the present invention, the serotonin transporter expressed in that host, the cells lysed, and the membranes from those cells used to screen compounds for competitive binding to the serotonin transporter with a labelled compound which binds to the serotonin transporter such as tritiated paroxetine or desimipramine. Assays in which such procedures may be carried out are well known, as illustrated by the Examples below. By selection of host cells which do not ordinarily express another transporter protein such as the noradrenaline transporter, GABA transporter, and/or dopamine transporter, preparations free of extraneous factors can be obtained. Further, the presence of a vesicular transport system for serotonin can be avoided by selecting as host cells cells which lack synaptic vesicles. Such assay systems have not heretofore been available.

Cloned genes of the present invention, and oligonucleotides derived therefrom, are useful for screening for restriction fragment length polymorphism (RFLP) associated with certain disorders.

Oligonucleotides of the present invention are useful as diagnostic tools for probing serotonin transporter gene expression in various tissues. For example, tissue can be probed in situ with oligonucleotide probes carrying detectable groups (i.e., "labelled") by conventional autoradiography techniques to investigate native expression of this transporter or pathological conditions relating thereto (e.g., human genetic disorders). This can be done routinely by temperature gradient electrophoresis. In addition, oligonucleotides of the present invention can be used to probe for other serotonin transporters subtypes or serotonin transporters in other species. Further, chromosomes can be probed to investigate the presence or absence of a serotonin transporter gene, and potential pathological conditions related thereto.

A variety of detectable groups can be employed to label antibodies and probes as disclosed herein, and the term "labelled" is used herein to refer to the conjugating or covalent bonding of any suitable detectable group, including enzymes (e.g., horseradish peroxidase, $\beta$-glucuronidase, alkaline phosphatase, and $\beta$-D-galactosidase), fluorescent labels (e.g., fluorescein, luciferase), and radiolabels (e.g., $^{14}C$, $^{131}I$, $^{3}H$, $^{32}P$, and $^{35}S$) to the compound being labelled. Techniques for labelling various compounds, including proteins, peptides, and antibodies, are well known. See, e.g., Morrison, *Methods in Enzymology* 32b, 103 (1974); Syvanen et al., *J. Biol. Chem.* 284, 3762 (1973); Bolton and Hunter, *Biochem. J.* 133, 529 (1973).

Antibodies which specifically bind to the serotonin transporter (i.e., antibodies which bind to a single antigenic site or epitope on the transporter) may be polyclonal or monoclonal in origin, but are preferably of monoclonal origin. Such antibodies are useful for the affinity purification of the serotonin transporter, and for the identification and assay of serotonin transporters in human tissue samples (e.g., post-mortem brain samples) or in peripheral platelet cells. The antibodies may be of any suitable species, such as rat, rabbit, or horse, but are generally of mammalian origin. The antibodies may be of any suitable immunoglobulin, such as IgG and IgM. Fragments of antibodies which retain the ability to specifically bind the serotonin transporter, such as F(ab')$_2$, F(ab'), and Fab fragments, are intended to be encompassed by the term "antibody" herein. The antibodies may be chimeric, as described by M. Walker et al., *Molecular Immunol.* 26, 403 (1989). Antibodies may be immobilized on a solid support of the type used as a packing in an affinity chromatography column, such as sepharose, silica, or glass beads, in accordance with known techniques.

Monoclonal antibodies which bind to the serotonin transporter are made by culturing a cell or cell line capable of producing the antibody under conditions suitable for the production of the antibody (e.g., by maintaining the cell line in HAT media), and then collecting the antibody from the culture (e.g., by precipitation, ion exchange chromatography, affinity chromatography, or the like). The antibodies may be generated in a hybridoma cell line in the widely used procedure described by G. Kohler and C. Milstein, *Nature* 256, 495 (1975), or may be generated with a recombinant vector in a suitable host cell such as *Escherichia coli* in the manner described by W. Huse et al., Generation of a Large Combinatorial Library of the Immunoglobulin Repertoire in Phage Lambda, *Science* 246, 1275 (1989).

Isolated and purified serotonin transporter of the present invention is useful in the rational design of drugs which interact with this transporter, and is useful as an immunogen for the production of antibodies which bind to the serotonin transporter. The serotonin transporter may be purified from cell membranes or lysed cell fractions containing the transporter, as described above, in accordance with known procedures, including column chromatography (e.g., ion exchange, gel filtration, electrophoresis, affinity chromatography, etc.), optionally followed by crystallization. See generally Enzyme Purification and Related Techniques, *Methods in Enzymology* 22, 233-577 (1977).

The present invention is explained in greater detail in the following non-limiting examples. In these examples, "$\mu g$" means micrograms, "ng" means nanograms, "$\mu Ci$" means microcuries, "ml" means milliliters, "SDS" means sodium dodecyl sulfate, "kb" means kilobase, "min" means minute, "hr" means hour, "mol" means mole "$\mu M$" means microMolar, and temperatures are given in degrees Centigrade unless otherwise indicated.

EXAMPLE 1

Production of Rodent Brain rMB6-25 cDNA by PCR

Using the polymerase chain reaction (PCR) (R. Saiki et al., *Science* 239, 487-494 (1988)) with degenerate oligonucleotides (R. Rathe, *J. Mol. Biol.* 183, 1-12 (1985)) derived from two highly conserved regions of recently cloned noradrenaline (hNAT) (T. Pacholczyk et al., *Nature* 350, 350-354 (1991)) and gamma-aminobutyric acid (rGAT1)(J. Guastella et al., *Science* 249, 1303-1306 (1990)) transporters, a large family of related gene products expressed in rodent brain were identified.

PCR reaction products obtained from amplification of rodent and human cDNA, which were of a size (~700 base pairs (bp)) predicted by hNAT and rGAT1, were purified, subcloned, and sequenced. After sequence analysis, 8 unique clones were identified. In pairwise sequence comparisons, most clones were equally similar to each other as to hNAT and rGAT1 with ~50-60% identity. However, another group, comprised of clones rTB2-5 and rMB6-25, were more closely related to hNAT, with 84% and 67% identity, respectively. Given the significant overlap in antagonist sensitivity among monoamine neurotransmitter transporters, see E. Richelson, *Mayo Clin. Proc.* 65, 1227-1236 (1990), we hypothesized that these two species could be partial clones encoding dopamine and serotonin (5HT) transporters. We accordingly focused our attention, in Example 2 below, on the size and regional distribution of rMB6-25 RNA in the rodent brain to determine the likely substrate for this transporter.

EXAMPLE 2

In Situ Hybridization Analysis of rMB6-25 cDNAs

This Example shows that the rMB6-25 cDNA hybridizes to a single 3.7 kb RNA restricted to rat midbrain and brainstem, where it is highly enriched within the serotonergic raphe complex.

For in situ hybridization experiments, synthetic [$^{35}$S]-labeled cRNA was synthesized with PCR fragment rMB6-25, cloned into the XbaI and XhoI sites of pBluescript SKII(-), from either the T3 promoter after plasmid linearization with XhoI (antisense cRNA) or from the T7 promoter after linearization with XbaI (sense cRNA). cRNA synthesis and in situ hybridization to 4% paraformaldehyde-fixed rat brain sections was conducted in accordance with known techniques. See R. Fremeau et al., *Proc. Natl. Acad. Sci. USA* 88, 3772-3776 (1991). cDNA derived from PCR fragment rMB6-25 (100 ng) was radiolabeled with [$^{32}$P]-labeled dCTP (50 $\mu$Ci) using random oligonucleotide primers and hybridized to a nylon (Zetaprobe, BioRad) transfer of total RNAs (20 $\mu$g) derived from rat tissues and rat and human cell lines. Blots were prehybridized at 42° C. in 50% formamide, 5XSSPE, 5X Denhardt's, 10% dextran sulfate, 1% SDS, and 100 $\mu$g/ml salmon sperm DNA for 2 hrs, probe added and hybridization continued for 14 hrs. Blot was rinsed with 2, 20 min 22° C. washes in 2XSSPE, 0.1% SDS, followed by a 1 hr rinse at 65° C. in 0.1X SSPE, 0.1% SDS, and then exposed to autoradiographic film with intensifying screen for 5 days. Positions of 18S (1950 kb) and 28S (4700 kb) ribosomal RNAs are noted. All lanes were equivalently loaded based on even intensity of ribosomal RNAs.

In situ hybridization analyses of endogenous RNA expression in slide-mounted sections of adult rat brain revealed a prominent and specific hybridization signal to radiolabeled antisense cRNA transcribed from rMB6-25 overlying dorsal and median subdivisions of the serotonergic midbrain raphe complex. See H. Steinbusch & R. Niewenhuys, in *Chemical Neuroanatomy*, 131-207 (P. Emson Ed., Raven Press, N.Y. 1983). Similarly, Northern hybridizations indicate the presence of a single 3.7 kb hybridizing RNA in rat midbrain and brainstem. Our inability to detect hybridization from total brain RNA underscores the restriction of gene expression for this putative transporter to cells of the mesencephalic and metencephalic raphe complex. Thus, the CNS distribution of hybridizing RNAs strongly suggests that rMB6-25 encodes a partial clone of the 5HT transporter. The adrenal RNA visualized in Northern analyses is unlikely to arise from cross-hybridization to the noradrenaline carrier as no RNAs were detected from the pheochromocytoma cells (PC12), derived from adrenal chromaffin cells, or human SK-N-SH neuroblastoma cells, both of which express high levels of the noradrenaline transporter. In this regard, 5HT has been detected in mast cells lining rat adrenal arterioles and in a population of medullary cells synthesizing adrenaline. See generally J. Hinson et al., *J. Endocrinol.* 121, 253-260 (1989); M. Holzworth & M. Brownfield, *Neuroendocrinol.* 41, 230-236 (1985); A. Verhofstad & G. Jonsson, *Neuroscience* 10, 1443-1453 (1983).

The properties of the adrenal RNA (equivalent size, high-stringency hybridization) lead us to hypothesize that 3.7 kb mRNAs with high sequence correspondence to PCR clone rMB6-25 encode both brain and peripheral 5HT transporters.

EXAMPLE 3

Isolation of Rat 5HT Transporter cDNA BS4E-10

This Example describes the isolation of a cDNA encoding the rat 5HT transporter. In brief, a synthetic antisense oligonucleotide corresponding to the poorly conserved amino acid sequence in the 5'end of PCR clone rMB6-25 was used to screen a rat brainstem cDNA library by plaque hybridization. See J. Sambrook et al., *Molecular Cloning: A Laboratory Manual*, 2d Ed. (Cold Spring Harbor Laboratory Press, Cold Spring Harbor, N.Y., 1989). One positive plaque from a total screen of $1.2 \times 10^6$ plaques was identified, purified, and the EcoR1 insert subcloned into pBluescript SKII− (Stratagene).

The conserved amino acid sequences NVWRFPY (SEQ ID NO:1) and WIDAATQ (SEQ ID NO:2) of hNAT and rGAT1 were used to design degenerate inosine (I)-substituted oligonucleotides of sequence 5'CCGCTCGAGAA(C/T)GT(G/C)TGGCG(C/G)TT(C/T)CC(A/G/C/T)TA3' (SEQ ID NO:3) and 5'GCTCTAGAGCTG(A/G)GTIGC(A/G)GC(A/G)TC(A/G)-A(T/G)CCA3' (SEQ ID NO:4), respectively (Underlined sequence indicates addition of 5' restriction sites for cloning). Oligonucleotides were combined with single-stranded, rat and human cDNAs, synthesized from poly(A)+- RNA with random hexamer primers (Amersham), into PCR reactions conducted with Taq polymerase for 30 cycles of 94°-1 min, 45°-2 min, 72°−3 min, with the final extension lengthened to 15 min. Products of ~700 bp, after phenol extraction and ethanol precipitation, were digested with EcoR1 to prevent recloning of rGAT1, which bears an EcoR1 site between the oligonucleotides utilized for amplification, and digested with Xba1 and Xho1 to produce staggered cloning ends. Samples were gel purified (GENECLEAN, Bio101), and ligated into Xba1-Xho1 digested pBluescript SKII(−) (Stratagene). Partial sequencing of double-stranded plasmid clones was achieved by dideoxynucleotide chain termination using Sequenase (US Biochem). Utilizing an end-labeled oligonucleotide derived from the poorly conserved region of the 5'end of PCR clone rMB6-25 TIMAIFG (SEQ ID NO:5), we isolated a single positive plaque in a screen of $1.2 \times 10^6$ bacteriophage from a rat brainstem cDNA library prepared in λgt10 (Clontech). The insert, designated BS4E-10, was liberated from purified bacteriophage with EcoR1 and ligated into EcoR1-digested pBluescript SKII(-). Dideoxynucleotide chain termination sequencing was achieved on both strands with Sequenase (US Biochem). Sequences obtained from two separate, partial cDNAs isolated from a rat midbrain cDNA library in a separate screen were also used to confirm the sequence and interpret compressions. MacVector DNA analysis software (IBI) was utilized for sequence assembly and analysis.

The nucleotide and deduced amino acid sequence of the rat 5HT transporter (rSERT) encoded by BS4E-10 is given as SEQ ID NO:6 and SEQ ID NO:7, respectively. Sequences from bases 279-974 match those obtained from the partial cDNA clone rMB6-25. The sequence of BS4E-10 reveals an 1821 bp open reading frame (ORF) within a 2278 bp cDNA. The first ATG present in the cDNA begins at nucleotide 48 and was assigned as the initiation codon due to adherence to the initiation consensus sequence of Kozak, *Nucleic Acids Res.* 15, 8125-8148 (1987). The ORF predicts a protein of 607 amino acids with a relative molecular mass of 68,000 ($M_r$ 68K) and is distinguished by the presence of 11-12 regions of significantly extended hydrophobicity suitable for the formation of transmembrane (TM) domains. See J. Kyte & R. Doolittle, *J. Molec. Biol.* 157, 105-132 (1982). Two canonical sites for N-linked glycosylation are present on a large hydrophilic domain between putative TM domains 3 and 4, in a similar location to those observed for a predicted extracellular loop in the cloned noradrenaline and GABA transporters. See T. Pacholczyk et al., supra; J. Guastella et al., supra; H. Nelson et al., *FEBS Lettr.* 269, 181-184 (1990). As with these carriers, the $NH_2$-terminus fails to score as a signal sequence for membrane insertion, suggesting its retention in the cytoplasm. See G. von Heijne, *Eur. J. Biochem.* 133, 17-21 (1983). One consensus site for cAMP-dependent protein kinase phosphorylation (B. Kemp & R. Pearson, *Trends. Biochem. Sci.* 15, 342-346, (1990)) is present near the end of the $NH_2$-terminus. Interestingly, 5HT transporters derived from a human placental choriocarcimoma cell line (JAR) exhibit cAMP-dependent regulation. See D. Cool et al., *J. Biol. Chem.* 266, 15750-15757 (1991).

EXAMPLE 4

Expression and Characterization of Rat 5HT Transporter cDNA BS4E-10 in HeLa Fibroblasts This example shows that transfection of a single 2.3 kb brainstem cDNA clone is sufficient to confer expression of a $Na^+$-dependent 5HT transporter (rSERT) upon nonneural cells, with transport selectively and potently antagonized by 5HT uptake-specific antidepressants, including paroxetine, citalopram, and fluoxetine.

The cDNA (BS4E-10) insert was excised from λgt10 with EcoR1 and subcloned in pBluescript SKII(-) (Stratagene) placing the presumptive amino terminus (determined from PCR amplification and sequencing) immediately downstream of the T7 RNA polymerase promoter. Cells ($10^5$/well) were infected with recombinant vaccinia virus strain VTF7-3 (T. Fuerst et al., *Proc. Natl. Acad. Sci. USA* 83, 8122-8126 (1986)), expressing T7 RNA polymerase as previously described (R. Blakely et al., *Analyt. Biochem.* 194, 302-308 (1991)), followed 30 min later by liposome-mediated (Lipofectin, BRL) transfection of the cDNA construct. Control transfections consisted of equivalent amounts of transfected vector alone. 5HT transport assays were conducted 8 hours after transfection as described for the analysis of the transfected NA carrier, utilizing 5-[1,2-$^3H(N)$]hydroxytryptamine creatine sulfate ([$^3H$]5HT, 20 nM, Dupont/New England Nuclear) as substrate in Krebs-Ringers-Tris-Hepes (KRTH) uptake media. Assays were terminated and washed with cold KRTH, cells solubilized with 1% SDS and accumulated radioactivity determined by scintillation counting. Data presented as CPM/well represent mean ±SEM of triplicate experiments. Sodium-dependence was determined by isotonic substitution of assay NaCl with cholineCl. Inhibition assays, performed in duplicate or triplicate, were conducted ±increasing concentrations of selected substrates and antagonists of 5HT, norepinephrine, and dopamine transport. Nonspecific transport was assessed with a parallel transfection of pBluescript for each assay and values subtracted from signals obtained with BS4E-10 cDNA. Inhibition data are presented as a percentage of 5HT uptake obtained with labeled substrate alone. Errors associated with independent experiments were less than 10% of mean values plotted. Dopamine, noradrenaline, adrenaline, and histamine ($K_I > 10$ μM) were ineffective in blocking 5HT transport induced by BS4E-10. Experiments with increasing concentrations of unlabeled 5HT yielded a Km of 1.5 μM and a Vmax of $6.7 \times 10^{-18}$ mol/cell/min.

Figure 1B:
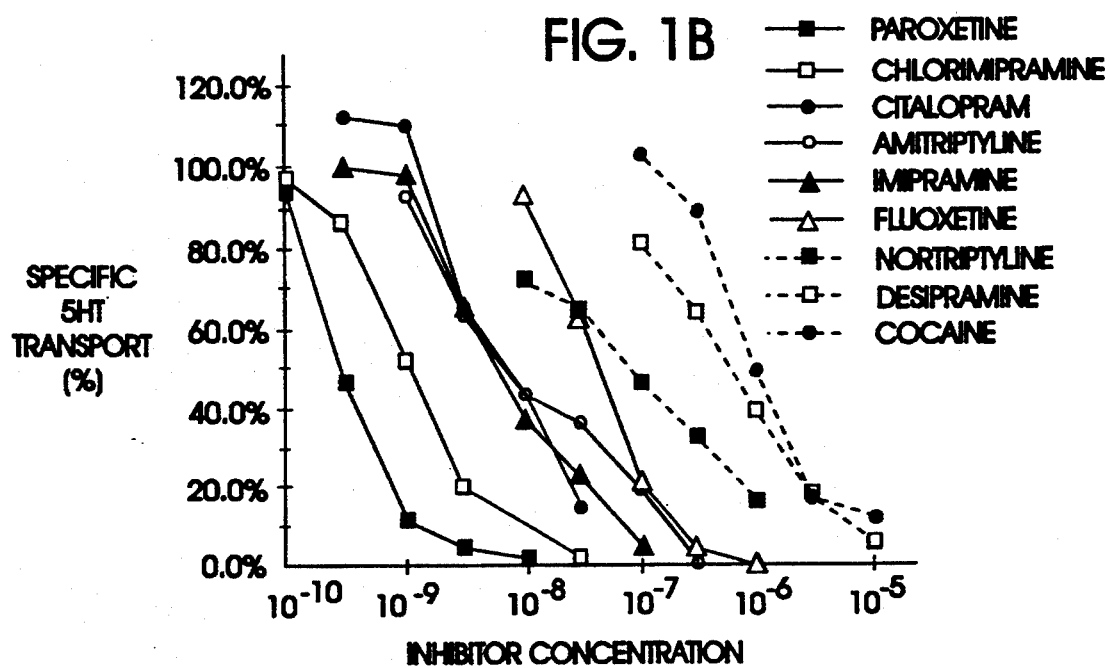
FIG. 1b shows the inhibition of 5HT transport in transfected cells by antagonists of monoamine transport.

FIG. 1a demonstrates that HeLa fibroblasts transfected with the BS4E-10 cDNA, though not with the plasmid vector alone, express $Na^+$-dependent, 5HT uptake. 5HT transport was found to be saturable with substrate (data not shown), exhibiting an apparent Km of 1.5 μM. Transport assays conducted in the presence of various uptake antagonists and substrates demonstrates a marked sensitivity of induced 5HT transport to tricyclic and heterocyclic antidepressants (FIG. 1b). The tertiary amine tricyclic antidepressants, amitriptyline and imipramine were significantly more potent antagonists ($K_I = 16.9$ and 18.7 nM, respectively) than their respective secondary amine congeners, nortriptyline and desipramine ($K_I = 73.5$ and 567 nM, respectively), giving a rank order potency of amitriptyline > imipramine > nortriptyline > desipramine. In contrast, the cloned NA transporter exhibits a reverse rank order potency of desipramine > nortriptyline > imipramine > amitriptyline. See T. Pacholczyk et al., supra. The order and magnitude of tricyclic potencies are generally equivalent to those obtained with serotonin transport studies in brain preparations. See R. Maxwell & H. White, in *Handbook of Psychopharmacology*, eds. L. L, Iversen, S. D, & Snyder, S. H., 83–155 (Plenum Press, New York, 1978)As with brain preparations, halogenation of imipramine to chlorimipramine increases potency for transport in transfected cells by >5 fold. Several of the nontricyclic antidepressants are considerably more selective for inhibition of endogenous 5HT over catecholamine transport, including fluoxetine, citalopram, and paroxetine. See L. Lemberger et al., *Clin. Pharmacol. Ther.* 23, 421–429 (1978); J. Hyttel et al., *Psychopharmacology* 51, 225–233 (1977); J. Buss Lassen, *Eur. J. Pharmacol.* 47, 351–358 (1978). In this regard, paroxetine has a $K_I$ of 0.39 nM for inhibition of 5HT transport activity after transfection with BS4E-10, nearly three orders of magnitude more potent than its inhibition of the cloned NA carrier. The nonselective monoamine transport antagonist cocaine (M. Ritz et al., *Life Sci.* 46, 635–645, (1990)) also blocked 5HT transport induced by the cloned cDNA, with predictably lower potency than observed for inhibition of cloned NA uptake. The selective DA and NA transport inhibitors, GBR12909 and mazindol, exhibited only weak potency for inhibition of 5HT uptake ($K_I = 3.9$ and 10.0 μM, respectively). Thus, the activity of the protein encoded by the cloned cDNA, hereafter referred to as rSERT, bears marked similarity in pharmacologic properties to the rat brain 5HT transporter, possessing high-affinity sites for both tricyclic and (the more selective) heterocyclic antidepressant antagonists.

EXAMPLE 5

Further Sequencing of Rat 5HT Transporter cDNA BS4E-10

On further sequencing a corrected sequence for rat 5HT transporter cDNA was obtained. While the sequence obtained in Example 3 was essentially correct and could be used as a probe to obtain rat 5HT transporter cDNA, further sequencing refined the knowledge of the actual sequence of rat 5HT transporter cDNA.

The nucleotide and deduced amino acid sequence of the rat 5HT transporter (rSERT) encoded by BS4E-10 is given as SEQ ID NO:8 and SEQ ID NO:9, respectively. Sequences from bases 279-974 match those obtained from the partial cDNA clone rMB6-25.

In an early sequence (Example 3) a gel compression was misread as two bases rather than one. The 120-CTGCAGTCCCCAGGCACAAG-140 should have been read as 120-CTGCAGTCCCCAGCACAAG-139. With this alteration, it was clear that the true start for translation was present in a reading frame upstream of the start site indicated in Example 3, in a region that had been presumed to be a 5'noncoding sequence. The open reading frame encoding the transporter extends from base 116 to base 2005 of the revised cDNA, an open reading frame of 1890 bp. The ORF predicts a protein of 630 amino acids with a relative molecular mass of 70,000 ($M_r$ 70K). Expression of this construct in HeLa cells in parallel experiments with the original cDNA (Example 4) resulted in equivalent properties (data not shown). The differences in translation products of the two clones do not result in detectable differences in transport properties. The ability to screen for other DNA is not affected.

EXAMPLE 6

Structural Model of Rat 5HT Transporter

Alignment of amino acid sequences encoding rat 5HT (rSERT), human noradrenaline (hNAT), and rat GABA (rGAT1) transporters were produced by iterative use of the BESTFIT routine of the Wisconsin GCG software package. J. Devereux et al., *Nucleic Acids Res.* 12, 387–395 (1984). In brief, this analysis showed ~31% of amino acid residues were absolutely conserved among all three carriers. A high degree of conservation among the three carriers between amino acids 76 and 98 was noted, where 17/23 residues are conserved.

Comparison of the predicted amino acid sequences encoding rSERT, the human NA transporter (hNAT), and the rat GABA transporter (rGAT1) demonstrates striking sequence conservation. Although rSERT is more closely related to hNAT than to rGAT1, with 50% (vs. 43%) absolutely conserved residues which rises to 72% (vs. 67%) similarity accepting conservative substitutions, ~30% of all residues are absolutely conserved across the three carriers. Many of these absolutely conserved residues are positioned in or adjacent to the TM domains and are likely to be involved in determining critical aspects of secondary structure required for ion binding and/or substrate translocation.

Figure 2:
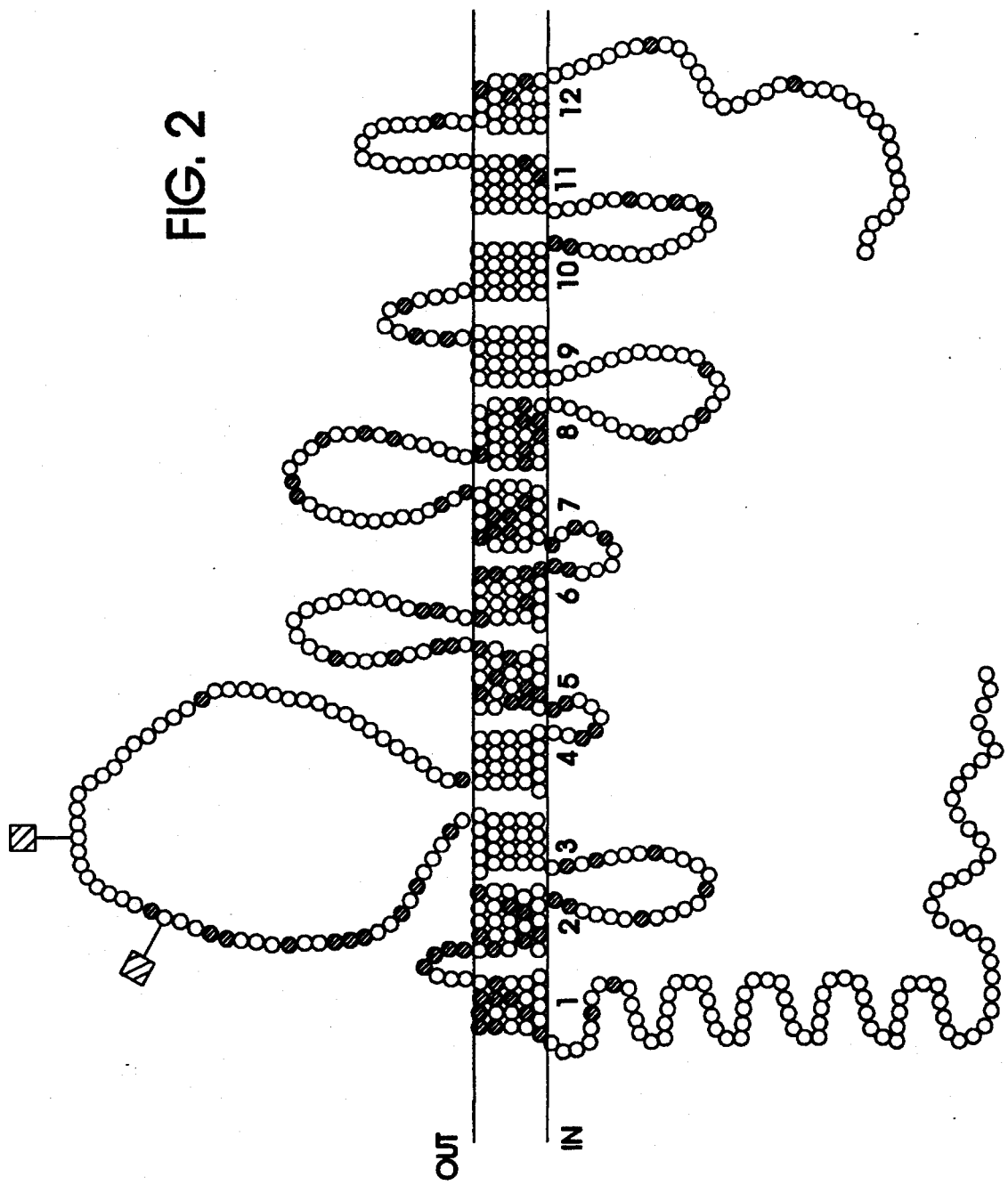
FIG. 2 provides a structural model for the serotonin transporter. Circles represent individual amino acids. Shaded circles reflect amino acids absolutely conserved between rSERT and hNAT, but not present in the related rGAT1, possibly involved in transport activities specific to noradrenaline and serotonin carriers such as the binding of tricyclic antidepressants. Note the localization of conserved residues in certain transmembrane domains relative to predicted cytoplasmic and extracellular domains. Black boxes indicate sugars attached to canonical sites for N-linked glycosylation.

To gain insight into the amino acids likely to be involved in monoamine transporter-specific functions, such as binding of tricyclic antidepressants and cocaine, we determined the positions of absolutely conserved residues among rSERT and hNAT, but which were not conserved in rGAT1 as the latter transporter lacks sensitivity to these agents. Superimposed on a preliminary structural model of rSERT (FIG. 2), these residues cluster prominently in several putative transmembrane domains, particularly TM domains 5–7 (Compare with TM9 and 12). Interestingly, only one acidic residue (Asp 75, TM1) in the transmembrane domains is conserved between rSERT and hNAT, but absent from rGAT1. Most transport antagonists are believed to occupy sites overlapping the substrate binding site. See P. Andersen, *Eur. J. Pharm.* 166, 493–504 (1989); D. Graham et al., *Biochem. Pharmacol.* 38, 3819–3826 (1989); J. Marcusson et al., *Psychopharmacology* 99, 17–21 (1989). A negatively charged residue may be involved in the binding of polar amino groups of substrates and antagonists to monoamine transporters. See R. Maxwell & H. White, supra; B. Koe, *J. Pharm. Exp. Ther.* 199, 649–661 (1976). Thus we suggest that monoamine neurotransmitter transporters bind their substrates and antagonists in the plane of the membrane, possibly involving determinants of TM domains 1, 5–7. A similar extended intramembrane pocket has been proposed for G-protein coupled receptor binding of neurotransmitters and antagonists. See C. Strader et al., *FASEB J.* 3, 1825–1832 (1989); B. Kobilka et al., *Science* 240, 1310–1316 (1988). Outside of the aforementioned identities with noradrenaline and GABA transporters, no significant identities were obtained in sequence comparisons with other members of the GenBank data base including receptors, the $Na^+$/glucose and $Na^+$/proline transporters, or facilitated carriers.

In summary, we have identified a single brain cDNA sufficient to form a fully functional 5HT transporter in nonneuronal cells. A higher resolution definition of the spatial organization of important residues in the 5HT transporter should assist synthetic approaches toward more selective therapeutic agents. In this regard, the presence of high-affinity tricyclic antidepressant binding sites on both rSERT and hNAT should permit rapid progress in the elucidation of key residues defining antagonist selectivity. Several selective serotonin (5HT) transport inhibitors are presently being prescribed for the clinical management of depression, obsessive-compulsive disorder, panic disorder, bulimia, and obesity. R. Fuller & D. Wong, *Ann. NY. Acad. Sci.* 600, 69–80 (1990). The cloning of rSERT provides an immediate tool for the direct study of transcriptional and posttranslational regulation of the 5HT transporter in animal models and provides a means for the identification of a human homolog, suitable for an assessment of potential 5HT transporter genetic disturbances underlying neuropsychiatric disorders.

EXAMPLE 7

Cloning of Human 5HT Transporter cDNAs

This example describes the isolation of a cDNA encoding the human 5 HT transporter. The nucleotide and deduced amino acid sequence of the human 5HT transporter (hSERT) is given as SEQ ID NO:10 and SEQ ID NO:11.

Poly(A+)RNA, purified from a placental trophoblastic cell line (JAR; See Cool et al., *J. Biol. Chem.* 266, 15750–15757 (1991)) by the guanidium-isothocyanate/-cesium chloride method of Chirgwin (See MacDonald et al., *Meths. Enzymol.* 152, 219–227 (1987)) was converted to single stranded cDNA (Superscript, Gibco-BRL) and subjected to polymerase-chain reaction (PCR; See Saiki et al., *Science* 238, 487–494 (1988)); Hot-Tub DNA polymerase (Amersham) 30 cycles 94° C.-1 min, 42° C.-2 min, 72° C.-3 min, with 10 min extension times programmed on 1st and 30th cycles). Amplifications were conducted with degenerate oligonucleotides (5'-CCGCTCGAGAA(C/T)GT(G/C)TGGCG(C/G)TT(C/T)CC(A/G/C/T)TA-3', (SEQ. ID No. 3) and 5'-GCTCTAGAGCTG(A/G)GTIGC-(A/G)GC(A/G)TC(A/G)A(T/G)CCA-3') (SEQ. ID No. 4) designed to encode highly conserved sequences of NE and GABA transporters and that had been previously employed for the identification of the rat brain 5HT transporter (see Example 3 above). Following direct subcloning of PCR fragments (TA vector, Invitrogen), dideoxynucleotide sequencing (Sequenase, United States Biochemical) was performed on plasmid DNA to identify partial human 5HT transporter candidates. A synthetic 21mer oligonucleotide (5'-AAAGG-CAATGATGCAGATGGC-3'; SEQ ID NO:12), derived from the 5' end of the JAR cDNA, was 3' end labeled with $\gamma[^{32}P]ATP$ and polynucleotide kinase (See Sambrook et al., *Molecular Cloning: A Laboratory Manual*, 2d ed. (Cold Spring Harbor Laboratory Press, 1989), and used to screen a human placental cDNA library in $\gamma$ZAPII (Stratagene) by MagnaGraph (MSI) filter hybridization at 57° C. following manufacturer's protocols, substituting 0.5 mg/mL heparin sulfate to block nonspecific hybridization.

Three hybridizing clones were identified in a screen of $1.6 \times 10^6$ plaques, and, following plaque rescreening, were obtained as individual plasmids by in vivo excision. Restriction analysis and sequencing revealed two of these clones to be homologous to rSERT and to be identical with each other except for the presence of distinct deletions in each cDNA. Initial sequence of one of these revealed an open reading frame in register with the amended sequence of the rat 5HT transporter with absolutely conserved amino and carboxy termini, and additional 5' and 3' noncoding sequences. Transfection of this cDNA into HeLa cells, however, failed to confer 5HT transport function, raising the possibility that a nonsense mutation, deletion or recombination had occurred during construction, amplification, or excision of the library. Full sequence of the cDNA revealed a 103 bp deletion, comprising amino acids 516–550 of the rat transporter. A second cDNA possessed the missing region, however, it lacked 168 bp of sequence possessed by clone 1 immediately 3' of the point where the deletion in clone 1 had occurred. Restriction mapping and direct sequencing demonstrated the two clones to be identical in regions of overlap except for these missing sequences. Therefore, we adopted a recombination PCR approach (See Kriegler, *Gene Transfer and Expression: A Laboratory Manual*, Stockton Press, NY (1990) to ligate in-frame the two pieces possessed uniquely by the two cDNAs, which was subsequently transferred back into the original clone at convenient restriction sites. The resultant cDNA was resequenced to confirm that the construction reproduced completely the sequence of both clones.

EXAMPLE 8

Expression of hSERT in Transfected Cells

This example shows that the human cDNA identified in Example 7 encodes a high affinity, $Na^+$ and $Cl^-$ dependent 5HT transporter. A 2158 bp EcoRI/ApaI fragment of the reconstructed cDNA, containing 72 bp of 5' noncoding and 196 bp of 3' noncoding sequence, was subcloned into pBluescript KSII- to place the translation initiation codon 3' to the plasmid-encoded T7 RNA polymerase promoter. Plasmid (1 μg) was subsequently transfected into HeLa cells (100,000–200,000-/well of a 24 well plate) by liposome-mediated transfection (Lipofectin, GIBCO/BRL) previously infected with recombinant (VTF7-3) vaccinia virus encoding T7 RNA polymerase at 10 pfu, See Blakely et al., *Anal. Biochem.* 194, 302–308 (1991). Transport assays (15 min, 37° C. unless indicated) with 20 nM 5-[1,2-$^3$H(N)]hydroxytryptamine creatinine sulfate ([$^3$H]5HT, DuPont/NEN), 100 μM pargyline and L-ascorbate, were performed 8–12 hrs following transfection in Krebs/-Ringers/HEPES (KRH) buffer (120 mM NaCl, 4.7 mM KCl, 2.2 mM $CaCl_2$, 1.2 mM $MgSO_4$, 1.2 mM $KH_2PO_4$, 10 mM HEPES, pH 7.4) as previously described (see Blakely et al., *Nature*, 354, 66–70 (1991)). Nonspecific [$^3$H]5HT transport was assessed in parallel transfections with the plasmid vector and subtracted from the data. Sodium dependence of 5HT transport was assessed by isotonic substitution of NaCl with choline CL, while Cl-dependence was assessed in media substituted with Na-gluconate, Kgluconate, and $CaNO_3$. Substrate $K_m$ and inhibitor $K_I$ values of antagonists were determined by nonlinear weighted least-square fits (Kaleidagraph) of concentration/uptake profiles performed in triplicate, adjusting for substrate concentration as provided by Cheng and Prusoff, *Biochem. Pharmacol.* 22, 3099–3108 (1973). Values are provided ±SEM. Paroxetine was a gift from Beecham Pharmaceuticals, fluoxetine from Eli-Lilly Co., and RTI-55 (3β-[4-iodophenyl]tropan-2β-carboxylic acid methyl ester tartrate) from F.Ivy Carrol. Nomifensine was obtained from Research Biochemicals Inc. All other compounds were obtained from Sigma.

cDNA transfected cells, but not control cells transfected with the vector alone, rapidly accumulate 5HT in a Na+-dependent manner to a level similar to that observed with parallel rSERT transfections (data not shown). Transport is abolished (0.3±0.01% of control levels) when identical incubations were conducted in Cl-free media, verifying a requirement of induced 5HT transport on both extracellular Na+ and Cl−. Assays conducted with increasing concentrations of unlabeled 5HT confirmed saturability with respect to substrate (data not shown), with a single, high-affinity (Km=463 nM) interaction observed following Eadie-Hofstee data transformation. Uptake of radiolabeled 5HT is potently antagonized by well characterized 5HT transporter antagonists (data not shown). Thus the 5HT transport-selective antagonist paroxetine, but not the NE transport-selective antagonist nomifensine, potently inhibits 5HT uptake in transfected HeLa cells. Similarly, the tertiary amine tricyclic antidepressants, imipramine and amitriptyline are more potent than the secondary amine tricyclic desipramine, in contrast to their rank order potency for inhibition of NE transport (Desip>>Imip->Amitrip). The nonselective monoamine transport antagonists cocaine and amphetamine block 5HT transport at low micromolar concentrations, with the cocaine analogue RTI-55 exhibiting increased potency over cocaine, as also described for the rat brain DA transporter (See Boja et al., *Eur. J. Pharm.* 194, 133–134 (1991)). The biogenic amines norepinephrine, dopamine and histamine are only weak inhibitors of induced 5HT uptake, with $K_I$ values <10 μM. Thus, the identified human cDNA encodes a high-affinity, Na+ and Cl−-dependent, 5HT transporter, with antagonist specificities established in native placental, platelet, and brain membrane preparations and is hereafter referred to as hSERT.

In the 2508 bp cDNA sequence of the largest hSERT cDNA an ORF of 1890 bp is present, encoding a polypeptide of 630 amino acids, identical in length to the corrected amino acid sequence of rSERT (see Example 5). The predicted start of translation possesses a good consensus for translation initiation (AAACATGG) following Kozak, *Cell* 44, 283–292 (1986). The encoded protein is predicted to have a core size of 70,320 (Mr) and an isoelectric point of 5.8. As expected for members of the GABA/NE transporter gene family (see Blakely, *Curr. Op. Psych.* 5, 69–73 (1992)), 12 regions of marked hydrophobicity (See Kyte and Doolittle, *J. Molec. Biol.* 157, 105–132 (1982)) are present in perfect register with those identified in the rat transporter. The absence of a hydrophobic membrane insertion sequence (see Von Heijne, *Eur. J. Biochem.* 133, 17–21 (1983)) in the protein's amino terminus and a folding model to accommodate 12 TM domains places both amino and carboxy termini in the cytoplasm, as modeled for rSERT (see Example 6). The proteins encoded by hSERT and rSERT possess 92% amino acid identity, with differences largely restricted to the amino-terminus where 20 out of 52 differences occur. Within the hSERT TM domains, only domains 4, 9, and 12 exhibit multiple (and nonconservative) amino acid changes amino acid substitutions relative to rSERT. Like the rat 5HT transporter, the large hydrophilic loop between TM3 and TM4 possesses two canonical sites for N-linked glycosylation. Several recognition sites for protein kinase A (PKA-motif R/K-XX-S/T) and protein kinase C (PKC-motif S/T-X-R/K) are found in hSERT (see Kennely and Krebs, *J. Biol. Chem.* 266, 15555,15558 (1991)), 5 of which are conserved with rSERT and 4 of these ($Ser^8$, $Ser^{13}$, $Ser^{277}$, $Thr^{603}$) lie in presumptive cytoplasmic domains. Interestingly, sequence identity between hSERT and rSERT is not confined to protein coding sequences, as the preceding 72 bp of 5' noncoding sequence and the 406 bp of 3' noncoding sequence exhibit conspicuous stretches of alignment, with 72% and 55% overall identity, respectively. In comparisons of hSERT amino acid sequence with other human and rodent members of the Na+/Cl-cotransporter gene family, hSERT is most closely related to the human norepinephrine transporter (48% AA identity) with which it shares antagonism by tricyclic antidepressants, and the rat dopamine transporter (44% AA identity), which, like the norepinephrine transporter, also binds cocaine. Other family members exhibit 35–39% identity.

EXAMPLE 9

Tissue and Chromosomal Localization of hSERT Gene

This example demonstrates the pattern of 5HT transporter expression in human tissue. RNA distribution and heterogeneity were evaluated by hybridization of blotted human poly(A+) RNAs (Clontech) using random-primed hSERT cDNA as probe. Labeling and hybridizations were conducted with the Megaprime hybridization system (Amersham) following manufacturer's protocols except for the addition of two high-stringency washes at 65° C. in 0.1X SSPE, 0.5% SDS. Following stripping of the blot, similar hybridizations were conducted with random-primed human β-actin cDNA to insure for equivalent RNA loading and transfer.

Somatic cell hybrid analysis was performed with both rat and human 5HT transporter cDNAs. A mapping panel consisting of 17 mouse-human (NA09925 - NA 09938, NA09940, NA10324, and NA10567) and 2 Chinese hamster—human (NA10611 and GM07298) hybrids was obtained from the National Institute of General Medical Services Mutant Cell Repository (NIGMS). Characterization and human chromosome content in these hybrids are described in detail in the NIGMS catalogue. Southern hybridization was performed as previously described (see Yang-Feng et al., *Am. J. Hum. Genet.* 37, 1117–1128 (1985)). For in situ hybridization, cDNA probe was nick-translated with [3H]dATP and [3H]dCTP to a specific activity of $3 \times 10^7$ CPM/$\mu$g. Hybridization to human metaphases, post-hybridization and emulsion autoradiography were carried out as previously described (see Yang-Feng et al., *Am. J. Hum. Genet.* 37, 1117–1128 (1985)). Chromosomes were G-banded using Wright's stain for silver grain analysis.

RNA hybridizations were performed with the hSERT cDNA probe at high stringency. Three hybridizing RNAs of 6.8 kb, 4.9 kb, and 3.0 kb were detected in poly(A+) RNA from human placenta which contains syncititotrophoblasts known to exhibit antidepressant- and cocaine-sensitive 5HT transport (See Balkovitz et al., *J. Biol. Chem.* 264, 2195–2198 (1989) and Cool et al., *Biochemistry* 29, 1818–1822 (1990)) but not in human skeletal muscle, liver, heart, and kidney, tissues lacking the 5HT carrier. Multiple hybridizing RNAs are also observed in human lung, wherein endothelial cells express an imipramine-sensitive 5HT transporter (see Lee and Fanburg, *Am. J. Physiol.* 250, C761–C765 (1986)). Control hybridization with a $\beta$-actin cDNA confirmed RNA integrity and loading equivalence (data not shown). Interestingly, hybridization of total human brain poly(A+) RNA failed to detect 5HT transporter transcripts, likely a result of small quantities of midbrain and brainstem RNA in the commercial preparations that we utilized for hybridizations. Similar findings, however, are observed in the rat where midbrain and brainstem dissections are required to obtain enriched RNA suitable for visualization of 5HT transporter mRNA. Additional hybridizations conducted with human brainstem and JAR RNA revealed a single major band in brainstem comigrating with the 4.0 kB species visualized in placenta and lung, while JAR cells exhibited the placental hybridization pattern (data not shown).

Southern blot analysis of 19 human and rodent somatic cell hybrids mapped the 5HT transporter gene to human chromosome 17. rSERT cDNA probe detected five mouse EcoRI fragments of 23, 6.7 5.8, 4.2, and 2.9 kB, two hamster hybridizing bands of 14 and 8.6 kB, and a 15 kB human fragment. The human cDNA probe detected two mouse, hamster and human specific fragments of 6.6 and 5.8 kB, 14 and 8.3 kB, and 15 and 5.3 kB, respectively (data not shown). Both human fragments were found to specifically segregate with chromosome 17. In situ hybridization revealed specific labeling at region q11–q12 of chromosome 17. Of 137 grains in 100 cells analyzed, 23 were located at 17q11–q12. No other chromosomal site was labeled above background. As only 90 bp precedes the single internal EcoRI site of our hSERT cDNA probe, the two large hybridizing EcoRI fragments likely arise from a hSERT gene interrupted by one or more introns.

The foregoing examples are illustrative of the present invention, and are not to be construed as limiting thereof. The invention is defined by the following claims, with equivalents of the claims to be included therein.

---

That which is claimed is:

1. Isolated DNA selected from the group consisting of:
   (a) isolated DNA comprising SEQ ID NO: 6;
   (b) isolated DNA which hybridizes to the complementary strand of isolated DNA of (a) above under stringent hybridization conditions represented by a wash stringency of 0.3 Molar NaCl, 0.03M sodium citrate, 0.1% SDS at 60° C., and which encodes a serotonin transporter; and
   (c) isolated DNA differing from the isolated DNAs of (a) and (b) above in codon sequence due to the degeneracy of the genetic code, and which encodes a serotonin transporter.

2. Isolated DNA according to claim 1 which encodes rat serotonin transporter.

3. Isolated DNA according to claim 1, which encodes the rat serotonin transporter given in SEQ ID NO:9.

4. A DNA vector comprising DNA according to claim 1.

5. A DNA vector according to claim 4, wherein said vector DNA comprises a plasmid.

6. A DNA vector according to claim 4, wherein said vector DNA comprises a virus.

7. A DNA vector according to claim 4, wherein said vector DNA comprises a baculovirus.

8. A transformed host cell containing a recombinant DNA sequence comprising vector DNA and DNA selected from the group consisting of:
   (a) isolated DNA consisting essentially of SEQ ID NO: 6; and
   (b) isolated DNA differing from the isolated DNA of (a) above in codon sequence due to the degeneracy of the genetic code, and which encodes a serotonin transporter.

9. A host cell containing a recombinant DNA sequence comprising vector DNA and DNA selected from the group consisting of:
   (a) isolated DNA consisting essentially of SEQ ID NO: 6; and
   (b) isolated DNA differing from the isolated DNA of (a) above in codon sequence due to the degeneracy of the genetic code, and which encodes a serotonin transporter,
said host cell capable of expressing the encoded serotonin transporter.

10. A host cell according to claim 9, wherein said host cell is a mammalian cell.

11. A host cell according to claim 9, wherein said host cell is an insect cell.

12. An oligonucleotide probe capable of selectively hybridizing, under stringent hybridization conditions represented by a wash stringency of 0.3 Molar NaCl, 0.03M sodium citrate, 0.1% SDS at 60° C., to a DNA consisting a portion of SEQ ID NO.10.

13. An oligonucleotide probe according to claim 12, which probe is capable of serving as a PCR extension primer.

14. An oligonucleotide probe according to claim 12, which probe is labelled with a detectable group.

15. An oligonucleotide probe according to claim 14, which detectable group is a radioactive atom.

* * * * *

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Asn Val Trp Arg Phe Pro Tyr
 1                    5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Trp Ile Asp Ala Ala Thr Gln
1               5

( 2 ) INFORMATION FOR SEQ ID NO:3:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

CCGCTCGAGA AYGTSTGGCG STTYCCNTA                                   29

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:4:

GCTCTAGAGC TGRGTNGCRG CRTCRAKCCA                                  30

( 2 ) INFORMATION FOR SEQ ID NO:5:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:5:

Thr Ile Met Ala Ile Phe Gly
1               5

( 2 ) INFORMATION FOR SEQ ID NO:6:

( i ) SEQUENCE CHARACTERISTICS:
        ( A ) LENGTH: 2278 base pairs
        ( B ) TYPE: nucleic acid
        ( C ) STRANDEDNESS: single
        ( D ) TOPOLOGY: linear ( i i ) MOLECULE TYPE: cDNA ( v i i i ) POSITION IN GENOME:
        ( C ) UNITS: 2278 basepairs ( i x ) FEATURE:
        ( A ) NAME/KEY: CDS
        ( B ) LOCATION: 48..1868

( x i ) SEQUENCE DESCRIPTION: SEQ ID NO:6:

```
TCAGAAAGTG CTGTCAGAGT GTAAGGACAG AGAGGACTGT CAAGAAA ATG GTG TTC        56
                                                    Met Val Phe
                                                     1

TAC AGA AGG GTG TCC CCA CCA CAG CGG ACA GGG CAG AGC CTA GCC AAA       104
Tyr Arg Arg Val Ser Pro Pro Gln Arg Thr Gly Gln Ser Leu Ala Lys
     5               10                  15

TAT CCA ATG GGT ACT CTG CAG TCC CCA GGC ACA AGT GCA GGG GAC GAA       152
Tyr Pro Met Gly Thr Leu Gln Ser Pro Gly Thr Ser Ala Gly Asp Glu
 20              25                  30                  35

GCT TCA CAC TCG ATC CCA GCT GCC ACC ACC ACC CTG GTG GCT GAG ATT       200
```

|  |  |  |  |  |  |  |  |  |  |  |  |  |  |  |  |
|---|---|---|---|---|---|---|---|---|---|---|---|---|---|---|---|
| Ala | Ser | His | Ser | Ile<br>40 | Pro | Ala | Ala | Thr<br>45 | Thr | Leu | Val | Ala | Glu<br>50 | Ile |  |
| CGC | CAA | GGG | GAG | CGG | GAG | ACC | TGG | GGC | AAG | AAG | ATG | GAT | TTC | CTC | CTG | 248 |
| Arg | Gln | Gly | Glu<br>55 | Arg | Glu | Thr | Trp | Gly<br>60 | Lys | Lys | Met | Asp | Phe<br>65 | Leu | Leu |
| TCC | GTC | ATT | GGC | TAT | GCC | GTG | GAC | CTG | GGC | AAC | ATC | TGG | CGG | TTT | CCT | 296 |
| Ser | Val | Ile<br>70 | Gly | Tyr | Ala | Val | Asp<br>75 | Leu | Gly | Asn | Ile | Trp | Arg<br>80 | Phe | Pro |
| TAC | ATA | TGC | TAC | CAG | AAT | GGC | GGA | GGG | GCC | TTC | CTC | CTC | CCT | TAT | ACC | 344 |
| Tyr | Ile<br>85 | Cys | Tyr | Gln | Asn | Gly<br>90 | Gly | Gly | Ala | Phe | Leu<br>95 | Leu | Pro | Tyr | Thr |
| ATC | ATG | GCC | ATT | TTC | GGG | GGG | ATC | CCG | CTC | TTT | TAC | ATG | GAG | CTC | GCA | 392 |
| Ile<br>100 | Met | Ala | Ile | Phe | Gly<br>105 | Gly | Ile | Pro | Leu | Phe<br>110 | Tyr | Met | Glu | Leu | Ala<br>115 |
| CTG | GGC | CAG | TAC | CAC | CGA | AAC | GGG | TGC | ATT | TCC | ATA | TGG | AGG | AAG | ATC | 440 |
| Leu | Gly | Gln | Tyr | His<br>120 | Arg | Asn | Gly | Cys | Ile<br>125 | Ser | Ile | Trp | Arg | Lys<br>130 | Ile |
| TGC | CCG | ATT | TTC | AAA | GGC | ATT | GGT | TAC | GCC | ATC | TGC | ATC | ATC | GCC | TTT | 488 |
| Cys | Pro | Ile | Phe<br>135 | Lys | Gly | Ile | Gly | Tyr<br>140 | Ala | Ile | Cys | Ile | Ile<br>145 | Ala | Phe |
| TAC | ATC | GCC | TCC | TAC | TAC | AAC | ACC | ATC | ATA | GCC | TGG | GCG | CTC | TAC | TAC | 536 |
| Tyr | Ile | Ala<br>150 | Ser | Tyr | Tyr | Asn | Thr<br>155 | Ile | Ile | Ala | Trp | Ala<br>160 | Leu | Tyr | Tyr |
| CTC | ATC | TCC | TCC | CTC | ACG | GAC | CGG | CTG | CCC | TGG | ACC | AGC | TGC | ACG | AAC | 584 |
| Leu | Ile<br>165 | Ser | Ser | Leu | Thr | Asp<br>170 | Arg | Leu | Pro | Trp | Thr<br>175 | Ser | Cys | Thr | Asn |
| TCC | TGG | AAC | ACT | GGC | AAC | TGC | ACC | AAC | TAC | TTC | GCC | CAG | GAC | AAC | ATC | 632 |
| Ser<br>180 | Trp | Asn | Thr | Gly | Asn<br>185 | Cys | Thr | Asn | Tyr | Phe<br>190 | Ala | Gln | Asp | Asn | Ile<br>195 |
| ACC | TGG | ACG | CTG | CAT | TCC | ACG | TCC | CCC | GCT | GAG | GAG | TTC | TAC | TTG | CGC | 680 |
| Thr | Trp | Thr | Leu | His<br>200 | Ser | Thr | Ser | Pro | Ala<br>205 | Glu | Glu | Phe | Tyr | Leu<br>210 | Arg |
| CAT | GTC | CTG | CAG | ATC | CAC | CAG | TCT | AAG | GGA | CTC | CAG | GAC | CTG | GGC | ACC | 728 |
| His | Val | Leu | Gln | Ile<br>215 | His | Gln | Ser | Lys | Gly<br>220 | Leu | Gln | Asp | Leu | Gly<br>225 | Thr |
| ATC | AGC | TGG | CAG | CTG | ACT | CTC | TGC | ATC | GTG | CTC | ATC | TTC | ACC | GTA | ATC | 776 |
| Ile | Ser | Trp<br>230 | Gln | Leu | Thr | Leu | Cys<br>235 | Ile | Val | Leu | Ile | Phe<br>240 | Thr | Val | Ile |
| TAC | TTT | AGC | ATC | TGG | AAA | GGC | GTC | AAA | ACA | TCT | GGC | AAG | GTG | GTG | TGG | 824 |
| Tyr | Phe<br>245 | Ser | Ile | Trp | Lys | Gly<br>250 | Val | Lys | Thr | Ser | Gly<br>255 | Lys | Val | Val | Trp |
| GTG | ACA | GCC | ACC | TTC | CCA | TAC | ATT | GTC | CTC | TCT | GTC | CTG | CTG | GTG | AGG | 872 |
| Val<br>260 | Thr | Ala | Thr | Phe | Pro<br>265 | Tyr | Ile | Val | Leu | Ser<br>270 | Val | Leu | Leu | Val | Arg<br>275 |
| GGG | GCC | ACC | CTT | CCT | GGA | GCC | TGG | AGA | GGG | GTC | GTC | TTC | TAC | TTG | AAA | 920 |
| Gly | Ala | Thr | Leu | Pro<br>280 | Gly | Ala | Trp | Arg | Gly<br>285 | Val | Val | Phe | Tyr | Leu<br>290 | Lys |
| CCC | AAC | TGG | CAG | AAA | CTC | TTG | GAG | ACA | GGG | GTG | TGG | GTA | GAT | GCC | GCC | 968 |
| Pro | Asn | Trp | Gln<br>295 | Lys | Leu | Leu | Glu | Thr<br>300 | Gly | Val | Trp | Val | Asp<br>305 | Ala | Ala |
| GCT | CAG | ATC | TTC | TTC | TCT | CTT | GGC | CCG | GGC | TTT | GGG | GTT | CTC | CTG | GCT | 1016 |
| Ala | Gln | Ile<br>310 | Phe | Phe | Ser | Leu | Gly<br>315 | Pro | Gly | Phe | Gly | Val<br>320 | Leu | Leu | Ala |
| TTT | GCT | AGC | TAC | AAC | AAG | TTC | AAC | AAC | AAC | TGT | TAC | CAA | GAT | GCC | CTG | 1064 |
| Phe | Ala | Ser<br>325 | Tyr | Asn | Lys | Phe | Asn<br>330 | Asn | Asn | Cys | Tyr | Gln<br>335 | Asp | Ala | Leu |
| GTG | ACC | AGT | GTG | GTG | AAC | TGC | ATG | ACA | AGC | TTC | GTC | TCT | GGC | TTC | GTC | 1112 |
| Val | Thr | Ser<br>340 | Val | Val | Asn | Cys<br>345 | Met | Thr | Ser | Phe | Val<br>350 | Ser | Gly | Phe | Val<br>355 |
| ATC | TTC | ACG | GTG | CTT | GGC | TAC | ATG | GCG | GAG | ATG | AGG | AAT | GAA | GAT | GTG | 1160 |
| Ile | Phe | Thr | Val | Leu<br>360 | Gly | Tyr | Met | Ala | Glu<br>365 | Met | Arg | Asn | Glu | Asp<br>370 | Val |

```
TCA GAG GTG GCC AAA GAC GCA GGC CCC AGC CTC CTC TTC ATC ACG TAT    1208
Ser Glu Val Ala Lys Asp Ala Gly Pro Ser Leu Leu Phe Ile Thr Tyr
            375             380                 385

GCA GAG GCA ATA GCC AAC ATG CCA GCA TCC ACG TTC TTT GCC ATC ATC    1256
Ala Glu Ala Ile Ala Asn Met Pro Ala Ser Thr Phe Phe Ala Ile Ile
        390             395                 400

TTC TTC CTC ATG TTA ATC ACG CTG GGA TTG GAC AGC ACG TTC GCA GGC    1304
Phe Phe Leu Met Leu Ile Thr Leu Gly Leu Asp Ser Thr Phe Ala Gly
    405             410                 415

CTG GAA GGT GTG ATC ACA GCT GTG CTG GAT GAG TTC CCT CAC ATC TGG    1352
Leu Glu Gly Val Ile Thr Ala Val Leu Asp Glu Phe Pro His Ile Trp
420             425                 430                 435

GCC AAG CGC AGG GAA TGG TTC GTG CTC ATC GTG GTC ATC ACG TGC GTC    1400
Ala Lys Arg Arg Glu Trp Phe Val Leu Ile Val Val Ile Thr Cys Val
                440                 445                 450

TTG GGA TCC CTG CTC ACA CTG ACG TCA GGA GGG GCA TAC GTG GTG ACT    1448
Leu Gly Ser Leu Leu Thr Leu Thr Ser Gly Gly Ala Tyr Val Val Thr
            455                 460                 465

CTG CTG GAG GAG TAT GCC ACG GGG CCA GCA GTG CTC ACC GTG GCC CTC    1496
Leu Leu Glu Glu Tyr Ala Thr Gly Pro Ala Val Leu Thr Val Ala Leu
        470                 475                 480

ATC GAG GCC GTC GCC GTG TCT TGG TTC TAT GGA ATC ACT CAG TTC TGC    1544
Ile Glu Ala Val Ala Val Ser Trp Phe Tyr Gly Ile Thr Gln Phe Cys
    485                 490                 495

AGC GAT GTG AAG GAG ATG CTG GGC TTC AGC CCG GGA TGG TTT TGG AGG    1592
Ser Asp Val Lys Glu Met Leu Gly Phe Ser Pro Gly Trp Phe Trp Arg
500                 505                 510                 515

ATC TGC TGG GTG GCC ATC AGC CCT CTG TTT CTC CTG TTC ATC ATT TGC    1640
Ile Cys Trp Val Ala Ile Ser Pro Leu Phe Leu Leu Phe Ile Ile Cys
                520                 525                 530

AGT TTT CTG ATG AGC CCA CCC CAG CTA CGG CTT TTC CAA TAC AAC TAT    1688
Ser Phe Leu Met Ser Pro Pro Gln Leu Arg Leu Phe Gln Tyr Asn Tyr
            535                 540                 545

CCC CAC TGG AGT ATC GTC TTG GGC TAC TGC ATA GGG ATG TCG TCC GTC    1736
Pro His Trp Ser Ile Val Leu Gly Tyr Cys Ile Gly Met Ser Ser Val
        550                 555                 560

ATC TGC ATC CCT ACC TAT ATC ATT TAT CGG CTG ATC AGC ACT CCG GGG    1784
Ile Cys Ile Pro Thr Tyr Ile Ile Tyr Arg Leu Ile Ser Thr Pro Gly
    565                 570                 575

ACA CTT AAG GAG CGC ATT ATT AAA AGT ATC ACT CCT GAA ACA CCC ACA    1832
Thr Leu Lys Glu Arg Ile Ile Lys Ser Ile Thr Pro Glu Thr Pro Thr
580                 585                 590                 595

GAA ATC CCG TGT GGG GAC ATC CGC ATG AAT GCT GTG TAACACACCC         1878
Glu Ile Pro Cys Gly Asp Ile Arg Met Asn Ala Val
                600                 605

TGGGAGAGGA CACCTCTTCC CAGCCACCTC TCTCAGCTCT GAAAAGCCCC ACTGGACTCC  1938

TCCCCTCTAA GCCAAGCCTG ATGAAGACAC GGTCCTAACC ACTATGGTGC CCAGACTCTT  1998

GTGGATTCCG ACCACTTCTT TCCGTGGACT CTCAGACATG CTACCACATT CGATGGTGAC  2058

ACCACTGAGC TGGCCTCTTG GACACGTCAG GGAGTGGAAG GAGGGATGAA CGCCACCCAG  2118

TCATCAGCTA GCTTCAGGTT TAGAATTAGG TCTGTGAGAG TCTGTATCAT GTTTTTGGTA  2178

AGATCATACT ACCCCGCATC TGTTAGCTTC TAAAGCCTTC AATGTTCATG AATACATAAA  2238

CCACCTAAGA GAAAACAGAG ATGTCTTGCT AGCCATATAT                        2278
```

( 2 ) INFORMATION FOR SEQ ID NO:7:

( i ) SEQUENCE CHARACTERISTICS:
        ( A ) LENGTH: 607 amino acids
        ( B ) TYPE: amino acid
        ( D ) TOPOLOGY: linear (ii) MOLECULE TYPE: protein (xi) SEQUENCE DESCRIPTION: SEQ ID NO:7:

| Met | Val | Phe | Tyr | Arg | Arg | Val | Ser | Pro | Pro | Gln | Arg | Thr | Gly | Gln | Ser |
|---|---|---|---|---|---|---|---|---|---|---|---|---|---|---|---|
| 1 | | | | 5 | | | | | 10 | | | | | 15 | |

| Leu | Ala | Lys | Tyr | Pro | Met | Gly | Thr | Leu | Gln | Ser | Pro | Gly | Thr | Ser | Ala |
|---|---|---|---|---|---|---|---|---|---|---|---|---|---|---|---|
| | | | 20 | | | | | 25 | | | | | 30 | | |

| Gly | Asp | Glu | Ala | Ser | His | Ser | Ile | Pro | Ala | Ala | Thr | Thr | Thr | Leu | Val |
|---|---|---|---|---|---|---|---|---|---|---|---|---|---|---|---|
| | | 35 | | | | | 40 | | | | | 45 | | | |

| Ala | Glu | Ile | Arg | Gln | Gly | Glu | Arg | Glu | Thr | Trp | Gly | Lys | Lys | Met | Asp |
|---|---|---|---|---|---|---|---|---|---|---|---|---|---|---|---|
| | 50 | | | | | 55 | | | | | 60 | | | | |

| Phe | Leu | Leu | Ser | Val | Ile | Gly | Tyr | Ala | Val | Asp | Leu | Gly | Asn | Ile | Trp |
|---|---|---|---|---|---|---|---|---|---|---|---|---|---|---|---|
| 65 | | | | | 70 | | | | | 75 | | | | | 80 |

| Arg | Phe | Pro | Tyr | Ile | Cys | Tyr | Gln | Asn | Gly | Gly | Gly | Ala | Phe | Leu | Leu |
|---|---|---|---|---|---|---|---|---|---|---|---|---|---|---|---|
| | | | | 85 | | | | | 90 | | | | | 95 | |

| Pro | Tyr | Thr | Ile | Met | Ala | Ile | Phe | Gly | Gly | Ile | Pro | Leu | Phe | Tyr | Met |
|---|---|---|---|---|---|---|---|---|---|---|---|---|---|---|---|
| | | | 100 | | | | | 105 | | | | | 110 | | |

| Glu | Leu | Ala | Leu | Gly | Gln | Tyr | His | Arg | Asn | Gly | Cys | Ile | Ser | Ile | Trp |
|---|---|---|---|---|---|---|---|---|---|---|---|---|---|---|---|
| | | 115 | | | | | 120 | | | | | 125 | | | |

| Arg | Lys | Ile | Cys | Pro | Ile | Phe | Lys | Gly | Ile | Gly | Tyr | Ala | Ile | Cys | Ile |
|---|---|---|---|---|---|---|---|---|---|---|---|---|---|---|---|
| | 130 | | | | | 135 | | | | | 140 | | | | |

| Ile | Ala | Phe | Tyr | Ile | Ala | Ser | Tyr | Tyr | Asn | Thr | Ile | Ile | Ala | Trp | Ala |
|---|---|---|---|---|---|---|---|---|---|---|---|---|---|---|---|
| 145 | | | | | 150 | | | | | 155 | | | | | 160 |

| Leu | Tyr | Tyr | Leu | Ile | Ser | Ser | Leu | Thr | Asp | Arg | Leu | Pro | Trp | Thr | Ser |
|---|---|---|---|---|---|---|---|---|---|---|---|---|---|---|---|
| | | | | 165 | | | | | 170 | | | | | 175 | |

| Cys | Thr | Asn | Ser | Trp | Asn | Thr | Gly | Asn | Cys | Thr | Asn | Tyr | Phe | Ala | Gln |
|---|---|---|---|---|---|---|---|---|---|---|---|---|---|---|---|
| | | | 180 | | | | | 185 | | | | | 190 | | |

| Asp | Asn | Ile | Thr | Trp | Thr | Leu | His | Ser | Thr | Ser | Pro | Ala | Glu | Glu | Phe |
|---|---|---|---|---|---|---|---|---|---|---|---|---|---|---|---|
| | | 195 | | | | | 200 | | | | | 205 | | | |

| Tyr | Leu | Arg | His | Val | Leu | Gln | Ile | His | Gln | Ser | Lys | Gly | Leu | Gln | Asp |
|---|---|---|---|---|---|---|---|---|---|---|---|---|---|---|---|
| | 210 | | | | | 215 | | | | | 220 | | | | |

| Leu | Gly | Thr | Ile | Ser | Trp | Gln | Leu | Thr | Leu | Cys | Ile | Val | Leu | Ile | Phe |
|---|---|---|---|---|---|---|---|---|---|---|---|---|---|---|---|
| 225 | | | | | 230 | | | | | 235 | | | | | 240 |

| Thr | Val | Ile | Tyr | Phe | Ser | Ile | Trp | Lys | Gly | Val | Lys | Thr | Ser | Gly | Lys |
|---|---|---|---|---|---|---|---|---|---|---|---|---|---|---|---|
| | | | | 245 | | | | | 250 | | | | | 255 | |

| Val | Val | Trp | Val | Thr | Ala | Thr | Phe | Pro | Tyr | Ile | Val | Leu | Ser | Val | Leu |
|---|---|---|---|---|---|---|---|---|---|---|---|---|---|---|---|
| | | | 260 | | | | | 265 | | | | | 270 | | |

| Leu | Val | Arg | Gly | Ala | Thr | Leu | Pro | Gly | Ala | Trp | Arg | Gly | Val | Val | Phe |
|---|---|---|---|---|---|---|---|---|---|---|---|---|---|---|---|
| | | 275 | | | | | 280 | | | | | 285 | | | |

| Tyr | Leu | Lys | Pro | Asn | Trp | Gln | Lys | Leu | Leu | Glu | Thr | Gly | Val | Trp | Val |
|---|---|---|---|---|---|---|---|---|---|---|---|---|---|---|---|
| | 290 | | | | | 295 | | | | | 300 | | | | |

| Asp | Ala | Ala | Ala | Gln | Ile | Phe | Phe | Ser | Leu | Gly | Pro | Gly | Phe | Gly | Val |
|---|---|---|---|---|---|---|---|---|---|---|---|---|---|---|---|
| 305 | | | | | 310 | | | | | 315 | | | | | 320 |

| Leu | Leu | Ala | Phe | Ala | Ser | Tyr | Asn | Lys | Phe | Asn | Asn | Asn | Cys | Tyr | Gln |
|---|---|---|---|---|---|---|---|---|---|---|---|---|---|---|---|
| | | | | 325 | | | | | 330 | | | | | 335 | |

| Asp | Ala | Leu | Val | Thr | Ser | Val | Val | Asn | Cys | Met | Thr | Ser | Phe | Val | Ser |
|---|---|---|---|---|---|---|---|---|---|---|---|---|---|---|---|
| | | | 340 | | | | | 345 | | | | | 350 | | |

| Gly | Phe | Val | Ile | Phe | Thr | Val | Leu | Gly | Tyr | Met | Ala | Glu | Met | Arg | Asn |
|---|---|---|---|---|---|---|---|---|---|---|---|---|---|---|---|
| | | 355 | | | | | 360 | | | | | 365 | | | |

| Glu | Asp | Val | Ser | Glu | Val | Ala | Lys | Asp | Ala | Gly | Pro | Ser | Leu | Leu | Phe |
|---|---|---|---|---|---|---|---|---|---|---|---|---|---|---|---|
| | 370 | | | | | 375 | | | | | 380 | | | | |

| Ile | Thr | Tyr | Ala | Glu | Ala | Ile | Ala | Asn | Met | Pro | Ala | Ser | Thr | Phe | Phe |
|---|---|---|---|---|---|---|---|---|---|---|---|---|---|---|---|
| 385 | | | | | 390 | | | | | 395 | | | | | 400 |

| Ala | Ile | Ile | Phe | Phe | Leu | Met | Leu | Ile | Thr | Leu | Gly | Leu | Asp | Ser | Thr |
|---|---|---|---|---|---|---|---|---|---|---|---|---|---|---|---|
| | | | | 405 | | | | | 410 | | | | | 415 | |

| | | | | | | | | | | | | | | |
|---|---|---|---|---|---|---|---|---|---|---|---|---|---|---|
|Phe|Ala|Gly|Leu|Glu|Gly|Val|Ile|Thr|Ala|Val|Leu|Asp|Glu|Phe|Pro|
| | | |420| | | |425| | | |430| | | |
|His|Ile|Trp|Ala|Lys|Arg|Arg|Glu|Trp|Phe|Val|Leu|Ile|Val|Val|Ile|
| | |435| | | |440| | | |445| | | | |
|Thr|Cys|Val|Leu|Gly|Ser|Leu|Leu|Thr|Leu|Thr|Ser|Gly|Gly|Ala|Tyr|
| |450| | | |455| | | |460| | | | | |
|Val|Val|Thr|Leu|Leu|Glu|Glu|Tyr|Ala|Thr|Gly|Pro|Ala|Val|Leu|Thr|
|465| | | |470| | | |475| | | | | |480|
|Val|Ala|Leu|Ile|Glu|Ala|Val|Ala|Val|Ser|Trp|Phe|Tyr|Gly|Ile|Thr|
| | | |485| | | |490| | | | |495| | |
|Gln|Phe|Cys|Ser|Asp|Val|Lys|Glu|Met|Leu|Gly|Phe|Ser|Pro|Gly|Trp|
| | |500| | | |505| | | | |510| | | |
|Phe|Trp|Arg|Ile|Cys|Trp|Val|Ala|Ile|Ser|Pro|Leu|Phe|Leu|Leu|Phe|
| |515| | | |520| | | |525| | | | | |
|Ile|Ile|Cys|Ser|Phe|Leu|Met|Ser|Pro|Pro|Gln|Leu|Arg|Leu|Phe|Gln|
|530| | | |535| | | |540| | | | | | |
|Tyr|Asn|Tyr|Pro|His|Trp|Ser|Ile|Val|Leu|Gly|Tyr|Cys|Ile|Gly|Met|
|545| | | |550| | | |555| | | | | |560|
|Ser|Ser|Val|Ile|Cys|Ile|Pro|Thr|Tyr|Ile|Ile|Tyr|Arg|Leu|Ile|Ser|
| | | |565| | | |570| | | | |575| | |
|Thr|Pro|Gly|Thr|Leu|Lys|Glu|Arg|Ile|Ile|Lys|Ser|Ile|Thr|Pro|Glu|
| | |580| | | |585| | | | |590| | | |
|Thr|Pro|Thr|Glu|Ile|Pro|Cys|Gly|Asp|Ile|Arg|Met|Asn|Ala|Val| |
| |595| | | |600| | | | |605| | | | |

( 2 ) INFORMATION FOR SEQ ID NO:8:

( i ) SEQUENCE CHARACTERISTICS:
        ( A ) LENGTH: 2415 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: CDS
        ( B ) LOCATION: 116..2005

( x i ) SEQUENCE DESCRIPTION: SEQ ID NO:8:

```
CCCCCTCGAG CTTTCCGTCT TGTCCCCATA ACCCGAGAGG AGATTCAAAC CAAGAACCAA        60

GAGCTAGCCT GGGTCCTCGG CAGATGGGAA TCCGCATCAC TTACTGACCA GCAGC ATG        118
                                                              Met
                                                               1
```

| | | | | | | | | | | | | | | | |
|---|---|---|---|---|---|---|---|---|---|---|---|---|---|---|---|
|GAG|ACC|ACA|CCC|TTG|AAT|TCA|CAG|AAA|GTG|CTG|TCA|GAG|TGT|AAG|GAC|166|
|Glu|Thr|Thr|Pro|Leu|Asn|Ser|Gln|Lys|Val|Leu|Ser|Glu|Cys|Lys|Asp| |
| | | |5| | | | |10| | | | |15| | |
|AGA|GAG|GAC|TGT|CAA|GAA|AAT|GGT|GTT|CTA|CAG|AAG|GGT|GTC|CCC|ACC|214|
|Arg|Glu|Asp|Cys|Gln|Glu|Asn|Gly|Val|Leu|Gln|Lys|Gly|Val|Pro|Thr| |
| | |20| | | | |25| | | | |30| | | |
|ACA|GCG|GAC|AGG|GCA|GAG|CCT|AGC|CAA|ATA|TCC|AAT|GGG|TAC|TCT|GCA|262|
|Thr|Ala|Asp|Arg|Ala|Glu|Pro|Ser|Gln|Ile|Ser|Asn|Gly|Tyr|Ser|Ala| |
| |35| | | | |40| | | | |45| | | | |
|GTC|CCC|AGC|ACA|AGT|GCA|GGG|GAC|GAA|GCT|TCA|CAC|TCG|ATC|CCA|GCT|310|
|Val|Pro|Ser|Thr|Ser|Ala|Gly|Asp|Glu|Ala|Ser|His|Ser|Ile|Pro|Ala| |
|50| | | | |55| | | | |60| | | | |65| |
|GCC|ACC|ACC|ACC|CTG|GTG|GCT|GAG|ATT|CGC|CAA|GGG|GAG|CGG|GAG|ACC|358|
|Ala|Thr|Thr|Thr|Leu|Val|Ala|Glu|Ile|Arg|Gln|Gly|Glu|Arg|Glu|Thr| |
| | | |70| | | | |75| | | | |80| | | |
|TGG|GGC|AAG|AAG|ATG|GAT|TTC|CTC|CTG|TCC|GTC|ATT|GGC|TAT|GCC|GTG|406|
|Trp|Gly|Lys|Lys|Met|Asp|Phe|Leu|Leu|Ser|Val|Ile|Gly|Tyr|Ala|Val| |

|  |  |
|---|---|
| GAC CTG GGC AAC ATC TGG CGG TTT CCT TAC ATA TGC TAC CAG AAT GGC<br>Asp Leu Gly Asn Ile Trp Arg Phe Pro Tyr Ile Cys Tyr Gln Asn Gly<br>100              105              110 | 454 |
| GGA GGG GCC TTC CTC CTC CCT TAT ACC ATC ATG GCC ATT TTC GGG GGG<br>Gly Gly Ala Phe Leu Leu Pro Tyr Thr Ile Met Ala Ile Phe Gly Gly<br>115              120              125 | 502 |
| ATC CCG CTC TTT TAC ATG GAG CTC GCA CTG GGC CAG TAC CAC CGA AAC<br>Ile Pro Leu Phe Tyr Met Glu Leu Ala Leu Gly Gln Tyr His Arg Asn<br>130              135              140              145 | 550 |
| GGG TGC ATT TCC ATA TGG AGG AAG ATC TGC CCG ATT TTC AAA GGC ATT<br>Gly Cys Ile Ser Ile Trp Arg Lys Ile Cys Pro Ile Phe Lys Gly Ile<br>150              155              160 | 598 |
| GGT TAC GCC ATC TGC ATC ATC GCC TTT TAC ATC GCC TCC TAC TAC AAC<br>Gly Tyr Ala Ile Cys Ile Ile Ala Phe Tyr Ile Ala Ser Tyr Tyr Asn<br>165              170              175 | 646 |
| ACC ATC ATA GCC TGG GCG CTC TAC TAC CTC ATC TCC TCC CTC ACG GAC<br>Thr Ile Ile Ala Trp Ala Leu Tyr Tyr Leu Ile Ser Ser Leu Thr Asp<br>180              185              190 | 694 |
| CGG CTG CCC TGG ACC AGC TGC ACG AAC TCC TGG AAC ACT GGC AAC TGC<br>Arg Leu Pro Trp Thr Ser Cys Thr Asn Ser Trp Asn Thr Gly Asn Cys<br>195              200              205 | 742 |
| ACC AAC TAC TTC GCC CAG GAC AAC ATC ACC TGG ACG CTG CAT TCC ACG<br>Thr Asn Tyr Phe Ala Gln Asp Asn Ile Thr Trp Thr Leu His Ser Thr<br>210              215              220              225 | 790 |
| TCC CCC GCT GAG GAG TTC TAC TTG CGC CAT GTC CTG CAG ATC CAC CAG<br>Ser Pro Ala Glu Glu Phe Tyr Leu Arg His Val Leu Gln Ile His Gln<br>230              235              240 | 838 |
| TCT AAG GGA CTC CAG GAC CTG GGC ACC ATC AGC TGG CAG CTG ACT CTC<br>Ser Lys Gly Leu Gln Asp Leu Gly Thr Ile Ser Trp Gln Leu Thr Leu<br>245              250              255 | 886 |
| TGC ATC GTG CTC ATC TTC ACC GTA ATC TAC TTT AGC ATC TGG AAA GGC<br>Cys Ile Val Leu Ile Phe Thr Val Ile Tyr Phe Ser Ile Trp Lys Gly<br>260              265              270 | 934 |
| GTC AAA ACA TCT GGC AAG GTG GTG TGG GTG ACA GCC ACC TTC CCA TAC<br>Val Lys Thr Ser Gly Lys Val Val Trp Val Thr Ala Thr Phe Pro Tyr<br>275              280              285 | 982 |
| ATT GTC CTC TCT GTC CTG CTG GTG AGG GGG GCC ACC CTT CCT GGA GCC<br>Ile Val Leu Ser Val Leu Leu Val Arg Gly Ala Thr Leu Pro Gly Ala<br>290              295              300              305 | 1030 |
| TGG AGA GGG GTC GTC TTC TAC TTG AAA CCC AAC TGG CAG AAA CTC TTG<br>Trp Arg Gly Val Val Phe Tyr Leu Lys Pro Asn Trp Gln Lys Leu Leu<br>310              315              320 | 1078 |
| GAG ACA GGG GTG TGG GTA GAT GCC GCC GCT CAG ATC TTC TTC TCT CTT<br>Glu Thr Gly Val Trp Val Asp Ala Ala Ala Gln Ile Phe Phe Ser Leu<br>325              330              335 | 1126 |
| GGC CCG GGC TTT GGG GTT CTC CTG GCT TTT GCT AGC TAC AAC AAG TTC<br>Gly Pro Gly Phe Gly Val Leu Leu Ala Phe Ala Ser Tyr Asn Lys Phe<br>340              345              350 | 1174 |
| AAC AAC AAC TGT TAC CAA GAT GCC CTG GTG ACC AGT GTG GTG AAC TGC<br>Asn Asn Asn Cys Tyr Gln Asp Ala Leu Val Thr Ser Val Val Asn Cys<br>355              360              365 | 1222 |
| ATG ACA AGC TTC GTC TCT GGC TTC GTC ATC TTC ACG GTG CTT GGC TAC<br>Met Thr Ser Phe Val Ser Gly Phe Val Ile Phe Thr Val Leu Gly Tyr<br>370              375              380              385 | 1270 |
| ATG GCG GAG ATG AGG AAT GAA GAT GTG TCA GAG GTG GCC AAA GAC GCA<br>Met Ala Glu Met Arg Asn Glu Asp Val Ser Glu Val Ala Lys Asp Ala<br>390              395              400 | 1318 |
| GGC CCC AGC CTC CTC TTC ATC ACG TAT GCA GAG GCA ATA GCC AAC ATG<br>Gly Pro Ser Leu Leu Phe Ile Thr Tyr Ala Glu Ala Ile Ala Asn Met<br>405              410              415 | 1366 |

| | | | | | | | | | | | | | | | | |
|---|---|---|---|---|---|---|---|---|---|---|---|---|---|---|---|---|
| CCA | GCA | TCC | ACG | TTC | TTT | GCC | ATC | ATC | TTC | TTC | CTC | ATG | TTA | ATC | ACG | 1414 |
| Pro | Ala | Ser | Thr | Phe | Phe | Ala | Ile | Ile | Phe | Phe | Leu | Met | Leu | Ile | Thr | |
| | | 420 | | | | | 425 | | | | | 430 | | | | |
| CTG | GGA | TTG | GAC | AGC | ACG | TTC | GCA | GGC | CTG | GAA | GGT | GTG | ATC | ACA | GCT | 1462 |
| Leu | Gly | Leu | Asp | Ser | Thr | Phe | Ala | Gly | Leu | Glu | Gly | Val | Ile | Thr | Ala | |
| | 435 | | | | | 440 | | | | | 445 | | | | | |
| GTG | CTG | GAT | GAG | TTC | CCT | CAC | ATC | TGG | GCC | AAG | CGC | AGG | GAA | TGG | TTC | 1510 |
| Val | Leu | Asp | Glu | Phe | Pro | His | Ile | Trp | Ala | Lys | Arg | Arg | Glu | Trp | Phe | |
| 450 | | | | | 455 | | | | 460 | | | | | | 465 | |
| GTG | CTC | ATC | GTG | GTC | ATC | ACG | TGC | GTC | TTG | GGA | TCC | CTG | CTC | ACA | CTG | 1558 |
| Val | Leu | Ile | Val | Val | Ile | Thr | Cys | Val | Leu | Gly | Ser | Leu | Leu | Thr | Leu | |
| | | | | 470 | | | | | 475 | | | | | 480 | | |
| ACG | TCA | GGA | GGG | GCA | TAC | GTG | GTG | ACT | CTG | CTG | GAG | GAG | TAT | GCC | ACG | 1606 |
| Thr | Ser | Gly | Gly | Ala | Tyr | Val | Val | Thr | Leu | Leu | Glu | Glu | Tyr | Ala | Thr | |
| | | | 485 | | | | | 490 | | | | | 495 | | | |
| GGG | CCA | GCA | GTG | CTC | ACC | GTG | GCC | CTC | ATC | GAG | GCC | GTC | GCC | GTG | TCT | 1654 |
| Gly | Pro | Ala | Val | Leu | Thr | Val | Ala | Leu | Ile | Glu | Ala | Val | Ala | Val | Ser | |
| | | 500 | | | | | 505 | | | | | 510 | | | | |
| TGG | TTC | TAT | GGA | ATC | ACT | CAG | TTC | TGC | AGC | GAT | GTG | AAG | GAG | ATG | CTG | 1702 |
| Trp | Phe | Tyr | Gly | Ile | Thr | Gln | Phe | Cys | Ser | Asp | Val | Lys | Glu | Met | Leu | |
| | 515 | | | | | 520 | | | | | 525 | | | | | |
| GGC | TTC | AGC | CCG | GGA | TGG | TTT | TGG | AGG | ATC | TGC | TGG | GTG | GCC | ATC | AGC | 1750 |
| Gly | Phe | Ser | Pro | Gly | Trp | Phe | Trp | Arg | Ile | Cys | Trp | Val | Ala | Ile | Ser | |
| 530 | | | | | 535 | | | | 540 | | | | | | 545 | |
| CCT | CTG | TTT | CTC | CTG | TTC | ATC | ATT | TGC | AGT | TTT | CTG | ATG | AGC | CCA | CCC | 1798 |
| Pro | Leu | Phe | Leu | Leu | Phe | Ile | Ile | Cys | Ser | Phe | Leu | Met | Ser | Pro | Pro | |
| | | | | 550 | | | | | 555 | | | | | 560 | | |
| CAG | CTA | CGG | CTT | TTC | CAA | TAC | AAC | TAT | CCC | CAC | TGG | AGT | ATC | GTC | TTG | 1846 |
| Gln | Leu | Arg | Leu | Phe | Gln | Tyr | Asn | Tyr | Pro | His | Trp | Ser | Ile | Val | Leu | |
| | | | 565 | | | | | 570 | | | | | 575 | | | |
| GGC | TAC | TGC | ATA | GGG | ATG | TCG | TCC | GTC | ATC | TGC | ATC | CCT | ACC | TAT | ATC | 1894 |
| Gly | Tyr | Cys | Ile | Gly | Met | Ser | Ser | Val | Ile | Cys | Ile | Pro | Thr | Tyr | Ile | |
| | | 580 | | | | | 585 | | | | | 590 | | | | |
| ATT | TAT | CGG | CTG | ATC | AGC | ACT | CCG | GGG | ACA | CTT | AAG | GAG | CGC | ATT | ATT | 1942 |
| Ile | Tyr | Arg | Leu | Ile | Ser | Thr | Pro | Gly | Thr | Leu | Lys | Glu | Arg | Ile | Ile | |
| | 595 | | | | | 600 | | | | | 605 | | | | | |
| AAA | AGT | ATC | ACT | CCT | GAA | ACA | CCC | ACA | GAA | ATC | CCG | TGT | GGG | GAC | ATC | 1990 |
| Lys | Ser | Ile | Thr | Pro | Glu | Thr | Pro | Thr | Glu | Ile | Pro | Cys | Gly | Asp | Ile | |
| 610 | | | | | 615 | | | | 620 | | | | | | 625 | |
| CGC | ATG | AAT | GCT | GTG | TAACACACCC | TGGGAGAGGA | CACCTCTTCC | CAGCCACCTC | | | | | | | | 2045 |
| Arg | Met | Asn | Ala | Val | | | | | | | | | | | | |
| | | | | 630 | | | | | | | | | | | | |

| | |
|---|---|
| TCTCAGCTCT GAAAAGCCCC ACTGGACTCC TCCCTCTAA GCCAAGCCTG ATGAAGACAC | 2105 |
| GGTCCTAACC ACTATGGTGC CCAGACTCTT GTGGATTCCG ACCACTTCTT TCCGTGGACT | 2165 |
| CTCAGACATG CTACCACATT CGATGGTGAC ACCACTGAGC TGGCCTCTTG GACACGTCAG | 2225 |
| GGAGTGGAAG GAGGGATGAA CGCCACCCAG TCATCAGCTA GCTTCAGGTT TAGAATTAGG | 2285 |
| TCTGTGAGAG TCTGTATCAT GTTTTTGGTA AGATCATACT ACCCCGCATC TGTTAGCTTC | 2345 |
| TAAAGCCTTC AATGTTCATG AATACATAAA CCACCTAAGA GAAAACAGAG ATGTCTTGCT | 2405 |
| AGCCATATAT | 2415 |

( 2 ) INFORMATION FOR SEQ ID NO:9:

( i ) SEQUENCE CHARACTERISTICS:
        ( A ) LENGTH: 630 amino acids
        ( B ) TYPE: amino acid
        ( D ) TOPOLOGY: linear ( i i ) MOLECULE TYPE: protein ( x i ) SEQUENCE DESCRIPTION: SEQ ID NO:9:

```
Met Glu Thr Thr Pro Leu Asn Ser Gln Lys Val Leu Ser Glu Cys Lys
 1           5                  10                 15
Asp Arg Glu Asp Cys Gln Glu Asn Gly Val Leu Gln Lys Gly Val Pro
            20              25              30
Thr Thr Ala Asp Arg Ala Glu Pro Ser Gln Ile Ser Asn Gly Tyr Ser
         35              40              45
Ala Val Pro Ser Thr Ser Ala Gly Asp Glu Ala Ser His Ser Ile Pro
     50              55              60
Ala Ala Thr Thr Thr Leu Val Ala Glu Ile Arg Gln Gly Glu Arg Glu
 65              70              75                      80
Thr Trp Gly Lys Lys Met Asp Phe Leu Leu Ser Val Ile Gly Tyr Ala
             85              90                      95
Val Asp Leu Gly Asn Ile Trp Arg Phe Pro Tyr Ile Cys Tyr Gln Asn
             100             105             110
Gly Gly Gly Ala Phe Leu Leu Pro Tyr Thr Ile Met Ala Ile Phe Gly
         115             120             125
Gly Ile Pro Leu Phe Tyr Met Glu Leu Ala Leu Gly Gln Tyr His Arg
     130             135             140
Asn Gly Cys Ile Ser Ile Trp Arg Lys Ile Cys Pro Ile Phe Lys Gly
145             150             155                     160
Ile Gly Tyr Ala Ile Cys Ile Ile Ala Phe Tyr Ile Ala Ser Tyr Tyr
             165             170             175
Asn Thr Ile Ile Ala Trp Ala Leu Tyr Tyr Leu Ile Ser Ser Leu Thr
             180             185             190
Asp Arg Leu Pro Trp Thr Ser Cys Thr Asn Ser Trp Asn Thr Gly Asn
             195             200             205
Cys Thr Asn Tyr Phe Ala Gln Asp Asn Ile Thr Trp Thr Leu His Ser
210             215             220
Thr Ser Pro Ala Glu Glu Phe Tyr Leu Arg His Val Leu Gln Ile His
225             230             235                     240
Gln Ser Lys Gly Leu Gln Asp Leu Gly Thr Ile Ser Trp Gln Leu Thr
             245             250             255
Leu Cys Ile Val Leu Ile Phe Thr Val Ile Tyr Phe Ser Ile Trp Lys
             260             265             270
Gly Val Lys Thr Ser Gly Lys Val Val Trp Val Thr Ala Thr Phe Pro
         275             280             285
Tyr Ile Val Leu Ser Val Leu Leu Val Arg Gly Ala Thr Leu Pro Gly
     290             295             300
Ala Trp Arg Gly Val Val Phe Tyr Leu Lys Pro Asn Trp Gln Lys Leu
305             310             315                     320
Leu Glu Thr Gly Val Trp Val Asp Ala Ala Gln Ile Phe Phe Ser
             325             330             335
Leu Gly Pro Gly Phe Gly Val Leu Leu Ala Phe Ala Ser Tyr Asn Lys
         340             345             350
Phe Asn Asn Asn Cys Tyr Gln Asp Ala Leu Val Thr Ser Val Val Asn
         355             360             365
Cys Met Thr Ser Phe Val Ser Gly Phe Val Ile Phe Thr Val Leu Gly
370             375             380
Tyr Met Ala Glu Met Arg Asn Glu Asp Val Ser Glu Val Ala Lys Asp
385             390             395                     400
Ala Gly Pro Ser Leu Leu Phe Ile Thr Tyr Ala Glu Ala Ile Ala Asn
             405             410             415
Met Pro Ala Ser Thr Phe Phe Ala Ile Ile Phe Phe Leu Met Leu Ile
             420             425             430
Thr Leu Gly Leu Asp Ser Thr Phe Ala Gly Leu Glu Gly Val Ile Thr
```

```
                    435                        440                        445
Ala  Val  Leu  Asp  Glu  Phe  Pro  His  Ile  Trp  Ala  Lys  Arg  Arg  Glu  Trp
     450                      455                      460

Phe  Val  Leu  Ile  Val  Val  Ile  Thr  Cys  Val  Leu  Gly  Ser  Leu  Leu  Thr
465                      470                      475                      480

Leu  Thr  Ser  Gly  Gly  Ala  Tyr  Val  Val  Thr  Leu  Leu  Glu  Glu  Tyr  Ala
               485                      490                      495

Thr  Gly  Pro  Ala  Val  Leu  Thr  Val  Ala  Leu  Ile  Glu  Ala  Val  Ala  Val
               500                      505                      510

Ser  Trp  Phe  Tyr  Gly  Ile  Thr  Gln  Phe  Cys  Ser  Asp  Val  Lys  Glu  Met
          515                      520                      525

Leu  Gly  Phe  Ser  Pro  Gly  Trp  Phe  Trp  Arg  Ile  Cys  Trp  Val  Ala  Ile
     530                      535                      540

Ser  Pro  Leu  Phe  Leu  Leu  Phe  Ile  Ile  Cys  Ser  Phe  Leu  Met  Ser  Pro
545                      550                      555                      560

Pro  Gln  Leu  Arg  Leu  Phe  Gln  Tyr  Asn  Tyr  Pro  His  Trp  Ser  Ile  Val
                    565                      570                      575

Leu  Gly  Tyr  Cys  Ile  Gly  Met  Ser  Ser  Val  Ile  Cys  Ile  Pro  Thr  Tyr
               580                      585                      590

Ile  Ile  Tyr  Arg  Leu  Ile  Ser  Thr  Pro  Gly  Thr  Leu  Lys  Glu  Arg  Ile
          595                      600                      605

Ile  Lys  Ser  Ile  Thr  Pro  Glu  Thr  Pro  Thr  Glu  Ile  Pro  Cys  Gly  Asp
     610                      615                      620

Ile  Arg  Met  Asn  Ala  Val
625                      630
```

( 2 ) INFORMATION FOR SEQ ID NO:10:

( i ) SEQUENCE CHARACTERISTICS:
        ( A ) LENGTH: 2508 base pairs
        ( B ) TYPE: nucleic acid
        ( C ) STRANDEDNESS: single
        ( D ) TOPOLOGY: linear ( i i ) MOLECULE TYPE: cDNA ( v i i i ) POSITION IN GENOME:
        ( C ) UNITS: 2278 basepairs ( i x ) FEATURE:
        ( A ) NAME/KEY: CDS
        ( B ) LOCATION: 73..1962

( x i ) SEQUENCE DESCRIPTION: SEQ ID NO:10:

```
CAAATCCAAG CACCCAGAGA TCAATTGGGA TCCTTGGCAG ATGGACATCA GTGTCATTTA           60

CTAACCAGCA GG ATG GAG ACG ACG CCC TTG AAT TCT CAG AAG CAG CTA              108
              Met Glu Thr Thr Pro Leu Asn Ser Gln Lys Gln Leu
                1               5                   10

TCA GCG TGT GAA GAT GGA GAA GAT TGT CAG GAA AAC GGA GTT CTA CAG            156
Ser Ala Cys Glu Asp Gly Glu Asp Cys Gln Glu Asn Gly Val Leu Gln
             15                  20                  25

AAG GTT GTT CCC ACC CCA GGG GAC AAA GTG GAG TCC GGG CAA ATA TCC            204
Lys Val Val Pro Thr Pro Gly Asp Lys Val Glu Ser Gly Gln Ile Ser
 30                  35                  40

AAT GGG TAC TCA GCA GTT CCA AGT CCT GGT GCG GGA GAT GAC ACA CGG            252
Asn Gly Tyr Ser Ala Val Pro Ser Pro Gly Ala Gly Asp Asp Thr Arg
 45                  50                  55                  60

CAC TCT ATC CCA GCG ACC ACC ACC ACC CTA GTG GCT GAG CTT CAT CAA            300
His Ser Ile Pro Ala Thr Thr Thr Thr Leu Val Ala Glu Leu His Gln
                 65                  70                  75

GGG GAA CGG GAG ACC TGG GGC AAG AAG GTG GAT TTC CTT CTC TCA GTG            348
Gly Glu Arg Glu Thr Trp Gly Lys Lys Val Asp Phe Leu Leu Ser Val
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 80  |     |     |     |     | 85  |     |     |     |     | 90  |     |     |      |
| ATT | GGC | TAT | GCT | GTG | GAC | CTG | GGC | AAT | GTC | TGG | CGC | TTC | CCC | TAC | ATA | 396  |
| Ile | Gly | Tyr | Ala | Val | Asp | Leu | Gly | Asn | Val | Trp | Arg | Phe | Pro | Tyr | Ile |      |
|     |     | 95  |     |     |     |     | 100 |     |     |     |     | 105 |     |     |     |      |
| TGT | TAC | CAG | AAT | GGA | GGG | GGG | GCA | TTC | CTC | CTC | CCC | TAC | ACC | ATC | ATG | 444  |
| Cys | Tyr | Gln | Asn | Gly | Gly | Gly | Ala | Phe | Leu | Leu | Pro | Tyr | Thr | Ile | Met |      |
|     | 110 |     |     |     |     | 115 |     |     |     |     | 120 |     |     |     |     |      |
| GCC | ATT | TTT | GGG | GGA | ATC | CCG | CTC | TTT | TAC | ATG | GAG | CTC | GCA | CTG | GGA | 492  |
| Ala | Ile | Phe | Gly | Gly | Ile | Pro | Leu | Phe | Tyr | Met | Glu | Leu | Ala | Leu | Gly |      |
| 125 |     |     |     |     | 130 |     |     |     |     | 135 |     |     |     |     | 140 |      |
| CAG | TAC | CAC | CGA | AAT | GGA | TGC | ATT | TCA | ATA | TGG | AGG | AAA | ATC | TGC | CCG | 540  |
| Gln | Tyr | His | Arg | Asn | Gly | Cys | Ile | Ser | Ile | Trp | Arg | Lys | Ile | Cys | Pro |      |
|     |     |     |     | 145 |     |     |     |     | 150 |     |     |     |     | 155 |     |      |
| ATT | TTC | AAA | GGG | ATT | GGT | TAT | GCC | ATC | TGC | ATC | ATT | GCC | TTT | TAC | ATT | 588  |
| Ile | Phe | Lys | Gly | Ile | Gly | Tyr | Ala | Ile | Cys | Ile | Ile | Ala | Phe | Tyr | Ile |      |
|     |     |     | 160 |     |     |     |     | 165 |     |     |     |     | 170 |     |     |      |
| GCT | TCC | TAC | TAC | AAC | ACC | ATC | ATG | GCC | TGG | GCG | CTA | TAC | TAC | CTC | ATC | 636  |
| Ala | Ser | Tyr | Tyr | Asn | Thr | Ile | Met | Ala | Trp | Ala | Leu | Tyr | Tyr | Leu | Ile |      |
|     | 175 |     |     |     |     | 180 |     |     |     |     | 185 |     |     |     |     |      |
| TCC | TCC | TTC | ACG | GAC | CAG | CTG | CCC | TGG | ACC | AGC | TGC | AAG | AAC | TCC | TGG | 684  |
| Ser | Ser | Phe | Thr | Asp | Gln | Leu | Pro | Trp | Thr | Ser | Cys | Lys | Asn | Ser | Trp |      |
| 190 |     |     |     |     | 195 |     |     |     |     | 200 |     |     |     |     |     |      |
| AAC | ACT | GGC | AAC | TGC | ACC | AAT | TAC | TTC | TCC | GAG | GAC | AAC | ATC | ACC | TGG | 732  |
| Asn | Thr | Gly | Asn | Cys | Thr | Asn | Tyr | Phe | Ser | Glu | Asp | Asn | Ile | Thr | Trp |      |
| 205 |     |     |     | 210 |     |     |     |     | 215 |     |     |     |     | 220 |     |      |
| ACC | CTC | CAT | TCC | ACG | TCC | CCT | GCT | GAA | GAA | TTT | TAC | ACG | CGC | CAC | GTC | 780  |
| Thr | Leu | His | Ser | Thr | Ser | Pro | Ala | Glu | Glu | Phe | Tyr | Thr | Arg | His | Val |      |
|     |     |     |     | 225 |     |     |     |     | 230 |     |     |     |     | 235 |     |      |
| CTG | CAG | ATC | CAC | CGG | TCT | AAG | GGG | CTC | CAG | GAC | CTG | GGG | GGC | ATC | AGC | 828  |
| Leu | Gln | Ile | His | Arg | Ser | Lys | Gly | Leu | Gln | Asp | Leu | Gly | Gly | Ile | Ser |      |
|     |     |     | 240 |     |     |     |     | 245 |     |     |     |     | 250 |     |     |      |
| TGG | CAG | CTG | GCC | CTC | TGC | ATC | ATG | CTG | ATC | TTC | ACT | GTT | ATC | TAC | TTC | 876  |
| Trp | Gln | Leu | Ala | Leu | Cys | Ile | Met | Leu | Ile | Phe | Thr | Val | Ile | Tyr | Phe |      |
|     |     | 255 |     |     |     |     | 260 |     |     |     |     | 265 |     |     |     |      |
| AGC | ATC | TGG | AAA | GGC | GTC | AAG | ACC | TCT | GGC | AAG | GTG | GTG | TGG | GTG | ACA | 924  |
| Ser | Ile | Trp | Lys | Gly | Val | Lys | Thr | Ser | Gly | Lys | Val | Val | Trp | Val | Thr |      |
|     | 270 |     |     |     |     | 275 |     |     |     |     | 280 |     |     |     |     |      |
| GCC | ACC | TTC | CCT | TAT | ATC | ATC | CTT | TCT | GTC | CTG | CTG | GTG | AGG | GGT | GCC | 972  |
| Ala | Thr | Phe | Pro | Tyr | Ile | Ile | Leu | Ser | Val | Leu | Leu | Val | Arg | Gly | Ala |      |
| 285 |     |     |     |     | 290 |     |     |     |     | 295 |     |     |     |     | 300 |      |
| ACC | CTC | CCT | GGA | GCC | TGG | AGG | GGT | GTT | CTC | TTC | TAC | TTG | AAA | CCC | AAT | 1020 |
| Thr | Leu | Pro | Gly | Ala | Trp | Arg | Gly | Val | Leu | Phe | Tyr | Leu | Lys | Pro | Asn |      |
|     |     |     |     | 305 |     |     |     |     | 310 |     |     |     |     | 315 |     |      |
| TGG | CAG | AAA | CTC | CTG | GAG | ACA | GGG | GTG | TGG | ATA | GAT | GCA | GCC | GCT | CAG | 1068 |
| Trp | Gln | Lys | Leu | Leu | Glu | Thr | Gly | Val | Trp | Ile | Asp | Ala | Ala | Ala | Gln |      |
|     |     |     | 320 |     |     |     |     | 325 |     |     |     |     | 330 |     |     |      |
| ATC | TTC | TTC | TCT | CTT | GGT | CCG | GGC | TTT | GGG | GTC | CTG | CTG | GCT | TTT | GCT | 1116 |
| Ile | Phe | Phe | Ser | Leu | Gly | Pro | Gly | Phe | Gly | Val | Leu | Leu | Ala | Phe | Ala |      |
|     |     | 335 |     |     |     |     | 340 |     |     |     |     | 345 |     |     |     |      |
| AGC | TAC | AAC | AAG | TTC | AAC | AAC | AAC | TGC | TAC | CAA | GAT | GCC | CTG | GTG | ACC | 1164 |
| Ser | Tyr | Asn | Lys | Phe | Asn | Asn | Asn | Cys | Tyr | Gln | Asp | Ala | Leu | Val | Thr |      |
|     | 350 |     |     |     |     | 355 |     |     |     |     | 360 |     |     |     |     |      |
| AGC | GTG | GTG | AAC | TGC | ATG | ACG | AGC | TTC | GTT | TCG | GGA | TTT | GTC | ATC | TTC | 1212 |
| Ser | Val | Val | Asn | Cys | Met | Thr | Ser | Phe | Val | Ser | Gly | Phe | Val | Ile | Phe |      |
| 365 |     |     |     |     | 370 |     |     |     |     | 375 |     |     |     |     | 380 |      |
| ACA | GTG | CTC | GGT | TAC | ATG | GCT | GAG | ATG | AGG | AAT | GAA | GAT | GTG | TCT | GAG | 1260 |
| Thr | Val | Leu | Gly | Tyr | Met | Ala | Glu | Met | Arg | Asn | Glu | Asp | Val | Ser | Glu |      |
|     |     |     |     | 385 |     |     |     |     | 390 |     |     |     |     | 395 |     |      |
| GTG | GCC | AAA | GAC | GCA | GGT | CCC | AGC | CTC | CTC | TTC | ATC | ACG | TAT | GCA | GAA | 1308 |
| Val | Ala | Lys | Asp | Ala | Gly | Pro | Ser | Leu | Leu | Phe | Ile | Thr | Tyr | Ala | Glu |      |
|     |     |     | 400 |     |     |     |     | 405 |     |     |     |     | 410 |     |     |      |

| | | | | | | | | | | | | | | | | |
|---|---|---|---|---|---|---|---|---|---|---|---|---|---|---|---|---|
| GCG | ATA | GCC | AAC | ATG | CCA | GCG | TCC | ACT | TTC | TTT | GCC | ATC | ATC | TTC | TTT | 1356 |
| Ala | Ile | Ala | Asn | Met | Pro | Ala | Ser | Thr | Phe | Phe | Ala | Ile | Ile | Phe | Phe | |
| | | 415 | | | | | 420 | | | | | 425 | | | | |
| CTG | ATG | TTA | ATC | ACG | CTG | GGC | TTG | GAC | AGC | ACG | TTT | GCA | GGC | TTG | GAG | 1404 |
| Leu | Met | Leu | Ile | Thr | Leu | Gly | Leu | Asp | Ser | Thr | Phe | Ala | Gly | Leu | Glu | |
| | 430 | | | | | 435 | | | | | 440 | | | | | |
| GGG | GTG | ATC | ACG | GCT | GTG | CTG | GAT | GAG | TTC | CCA | CAC | GTC | TGG | GCC | AAG | 1452 |
| Gly | Val | Ile | Thr | Ala | Val | Leu | Asp | Glu | Phe | Pro | His | Val | Trp | Ala | Lys | |
| 445 | | | | | 450 | | | | | 455 | | | | | 460 | |
| CGC | CGG | GAG | CGG | TTC | GTG | CTC | GCC | GTG | GTC | ATC | ACC | TGC | TTC | TTT | GGA | 1500 |
| Arg | Arg | Glu | Arg | Phe | Val | Leu | Ala | Val | Val | Ile | Thr | Cys | Phe | Phe | Gly | |
| | | | | 465 | | | | | 470 | | | | | 475 | | |
| TCC | CTG | GTC | ACC | CTG | ACT | TTT | GGA | GGG | GCC | TAC | GTG | GTG | AAG | CTG | CTG | 1548 |
| Ser | Leu | Val | Thr | Leu | Thr | Phe | Gly | Gly | Ala | Tyr | Val | Val | Lys | Leu | Leu | |
| | | | 480 | | | | | 485 | | | | | 490 | | | |
| GAG | GAG | TAT | GCC | ACG | GGG | CCC | GCA | GTG | CTC | ACT | GTC | GCG | CTG | ATC | GAA | 1596 |
| Glu | Glu | Tyr | Ala | Thr | Gly | Pro | Ala | Val | Leu | Thr | Val | Ala | Leu | Ile | Glu | |
| | | 495 | | | | | 500 | | | | | 505 | | | | |
| GCA | GTC | GCT | GTG | TCT | TGG | TTC | TAT | GGC | ATC | ACT | CAG | TTC | TGC | AGG | GAC | 1644 |
| Ala | Val | Ala | Val | Ser | Trp | Phe | Tyr | Gly | Ile | Thr | Gln | Phe | Cys | Arg | Asp | |
| | 510 | | | | | 515 | | | | | 520 | | | | | |
| GTG | AAG | GAA | ATG | CTC | GGC | TTC | AGC | CCG | GGG | TGG | TTC | TGG | AGG | ATC | TGC | 1692 |
| Val | Lys | Glu | Met | Leu | Gly | Phe | Ser | Pro | Gly | Trp | Phe | Trp | Arg | Ile | Cys | |
| 525 | | | | | 530 | | | | | 535 | | | | | 540 | |
| TGG | GTG | GCC | ATC | AGC | CCT | CTG | TTT | CTC | CTG | TTC | ATC | ATT | TGC | AGT | TTT | 1740 |
| Trp | Val | Ala | Ile | Ser | Pro | Leu | Phe | Leu | Leu | Phe | Ile | Ile | Cys | Ser | Phe | |
| | | | | 545 | | | | | 550 | | | | | 555 | | |
| CTG | ATG | AGC | CCG | CCA | CAA | CTA | CGA | CTT | TTC | CAA | TAT | AAT | TAT | CCT | TAC | 1788 |
| Leu | Met | Ser | Pro | Pro | Gln | Leu | Arg | Leu | Phe | Gln | Tyr | Asn | Tyr | Pro | Tyr | |
| | | | 560 | | | | | 565 | | | | | 570 | | | |
| TGG | AGT | ATC | ATC | TTG | GGT | TAC | TGC | ATA | GGA | ACC | TCA | TCT | TTC | ATT | TGC | 1836 |
| Trp | Ser | Ile | Ile | Leu | Gly | Tyr | Cys | Ile | Gly | Thr | Ser | Ser | Phe | Ile | Cys | |
| | | 575 | | | | | 580 | | | | | 585 | | | | |
| ATC | CCC | ACA | TAT | ATA | GCT | TAT | CGG | TTG | ATC | ATC | ACT | CCA | GGG | ACA | TTT | 1884 |
| Ile | Pro | Thr | Tyr | Ile | Ala | Tyr | Arg | Leu | Ile | Ile | Thr | Pro | Gly | Thr | Phe | |
| | 590 | | | | | 595 | | | | | 600 | | | | | |
| AAA | GAG | CGT | ATT | ATT | AAA | AGT | ATT | ACC | CCA | GAA | ACA | CCA | ACA | GAA | ATT | 1932 |
| Lys | Glu | Arg | Ile | Ile | Lys | Ser | Ile | Thr | Pro | Glu | Thr | Pro | Thr | Glu | Ile | |
| 605 | | | | | 610 | | | | | 615 | | | | | 620 | |
| CCT | TGT | GGG | GAC | ATC | CGC | TTG | AAT | GCT | GTG | TAACACACTC | ACCGAGAGGA | | | | | 1982 |
| Pro | Cys | Gly | Asp | Ile | Arg | Leu | Asn | Ala | Val | | | | | | | |
| | | | | 625 | | | | | 630 | | | | | | | |

| | | | | |
|---|---|---|---|---|
| AAAAGGCTTC | TCCACAACCT | CCTCCTCCAG | TTCTGATGAG | GCACGCCTGC | CTTCTCCCCT | 2042 |
| CCAAGTGAAT | GAGTTCCAG | CTAAGCCTGA | TGATGGAAGG | GCCTTCTCCA | CAGGGACACA | 2102 |
| GTCTGGTGCC | CAGACTCAAG | GCCTCCAGCC | ACTTATTTCC | ATGGATTCCC | CTGGACATAT | 2162 |
| TCCATGGTA | GACTGTGACA | CAGCTGAGCT | GGCCTATTTT | GGACGTGTGA | GGATGTGGAT | 2222 |
| GGAGGTGATG | AAAACCACCC | TATCATCAGT | TAGGATTAGG | TTTAGAATCA | AGTCTGTGAA | 2282 |
| AGTCTCCTGT | ATCATTTCTT | GGTATGATCA | TTGGTATCTG | ATATCTGTTT | GCTTCTAAAG | 2342 |
| GTTTCACTGT | TCATGAATAC | GTAAACTGCG | TAGGAGAGAA | CAGGGATGCT | ATCTCGCTAG | 2402 |
| CCATATATTT | TCTGAGTAGC | ATATAGAATT | TTATTGCTGG | AATCTACTAG | AACCTTCTAA | 2462 |
| TCCATGTGCT | GCTGTGGCAT | CAGGAAAGGA | AGATGTAAGA | AGCTAA | | 2508 |

( 2 ) INFORMATION FOR SEQ ID NO:11:

( i ) SEQUENCE CHARACTERISTICS:
        ( A ) LENGTH: 630 amino acids
        ( B ) TYPE: amino acid
        ( D ) TOPOLOGY: linear (i i) MOLECULE TYPE: protein (x i) SEQUENCE DESCRIPTION: SEQ ID NO:11:

```
Met Glu Thr Thr Pro Leu Asn Ser Gln Lys Gln Leu Ser Ala Cys Glu
 1               5                  10                  15

Asp Gly Glu Asp Cys Gln Glu Asn Gly Val Leu Gln Lys Val Val Pro
            20                  25                  30

Thr Pro Gly Asp Lys Val Glu Ser Gly Gln Ile Ser Asn Gly Tyr Ser
            35                  40                  45

Ala Val Pro Ser Pro Gly Ala Gly Asp Asp Thr Arg His Ser Ile Pro
        50                  55                  60

Ala Thr Thr Thr Thr Leu Val Ala Glu Leu His Gln Gly Glu Arg Glu
65                  70                  75                  80

Thr Trp Gly Lys Lys Val Asp Phe Leu Leu Ser Val Ile Gly Tyr Ala
                85                  90                  95

Val Asp Leu Gly Asn Val Trp Arg Phe Pro Tyr Ile Cys Tyr Gln Asn
            100                 105                 110

Gly Gly Gly Ala Phe Leu Leu Pro Tyr Thr Ile Met Ala Ile Phe Gly
        115                 120                 125

Gly Ile Pro Leu Phe Tyr Met Glu Leu Ala Leu Gly Gln Tyr His Arg
130                 135                 140

Asn Gly Cys Ile Ser Ile Trp Arg Lys Ile Cys Pro Ile Phe Lys Gly
145                 150                 155                 160

Ile Gly Tyr Ala Ile Cys Ile Ile Ala Phe Tyr Ile Ala Ser Tyr Tyr
                165                 170                 175

Asn Thr Ile Met Ala Trp Ala Leu Tyr Tyr Leu Ile Ser Ser Phe Thr
            180                 185                 190

Asp Gln Leu Pro Trp Thr Ser Cys Lys Asn Ser Trp Asn Thr Gly Asn
        195                 200                 205

Cys Thr Asn Tyr Phe Ser Glu Asp Asn Ile Thr Trp Thr Leu His Ser
210                 215                 220

Thr Ser Pro Ala Glu Glu Phe Tyr Thr Arg His Val Leu Gln Ile His
225                 230                 235                 240

Arg Ser Lys Gly Leu Gln Asp Leu Gly Gly Ile Ser Trp Gln Leu Ala
                245                 250                 255

Leu Cys Ile Met Leu Ile Phe Thr Val Ile Tyr Phe Ser Ile Trp Lys
            260                 265                 270

Gly Val Lys Thr Ser Gly Lys Val Val Trp Val Thr Ala Thr Phe Pro
        275                 280                 285

Tyr Ile Ile Leu Ser Val Leu Leu Val Arg Gly Ala Thr Leu Pro Gly
290                 295                 300

Ala Trp Arg Gly Val Leu Phe Tyr Leu Lys Pro Asn Trp Gln Lys Leu
305                 310                 315                 320

Leu Glu Thr Gly Val Trp Ile Asp Ala Ala Ala Gln Ile Phe Phe Ser
                325                 330                 335

Leu Gly Pro Gly Phe Gly Val Leu Leu Ala Phe Ala Ser Tyr Asn Lys
            340                 345                 350

Phe Asn Asn Asn Cys Tyr Gln Asp Ala Leu Val Thr Ser Val Val Asn
        355                 360                 365

Cys Met Thr Ser Phe Val Ser Gly Phe Val Ile Phe Thr Val Leu Gly
370                 375                 380

Tyr Met Ala Glu Met Arg Asn Glu Asp Val Ser Glu Val Ala Lys Asp
385                 390                 395                 400

Ala Gly Pro Ser Leu Leu Phe Ile Thr Tyr Ala Glu Ala Ile Ala Asn
                405                 410                 415
```

```
Met Pro Ala Ser Thr Phe Phe Ala Ile Ile Phe Phe Leu Met Leu Ile
        420             425             430

Thr Leu Gly Leu Asp Ser Thr Phe Ala Gly Leu Glu Gly Val Ile Thr
        435             440                     445

Ala Val Leu Asp Glu Phe Pro His Val Trp Ala Lys Arg Arg Glu Arg
450                     455             460

Phe Val Leu Ala Val Val Ile Thr Cys Phe Phe Gly Ser Leu Val Thr
465             470                     475                 480

Leu Thr Phe Gly Gly Ala Tyr Val Val Lys Leu Leu Glu Glu Tyr Ala
            485                     490                 495

Thr Gly Pro Ala Val Leu Thr Val Ala Leu Ile Glu Ala Val Ala Val
        500             505                     510

Ser Trp Phe Tyr Gly Ile Thr Gln Phe Cys Arg Asp Val Lys Glu Met
        515             520                 525

Leu Gly Phe Ser Pro Gly Trp Phe Trp Arg Ile Cys Trp Val Ala Ile
    530             535                 540

Ser Pro Leu Phe Leu Leu Phe Ile Ile Cys Ser Phe Leu Met Ser Pro
545             550                 555                 560

Pro Gln Leu Arg Leu Phe Gln Tyr Asn Tyr Pro Tyr Trp Ser Ile Ile
            565                 570                 575

Leu Gly Tyr Cys Ile Gly Thr Ser Ser Phe Ile Cys Ile Pro Thr Tyr
        580                     585                 590

Ile Ala Tyr Arg Leu Ile Ile Thr Pro Gly Thr Phe Lys Glu Arg Ile
        595             600             605

Ile Lys Ser Ile Thr Pro Glu Thr Pro Thr Glu Ile Pro Cys Gly Asp
610                     615             620

Ile Arg Leu Asn Ala Val
625             630
```

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:12:

AAAGGCAATG ATGCAGATGG C       21